United States Patent
Clement et al.

(10) Patent No.: US 11,208,630 B2
(45) Date of Patent: Dec. 28, 2021

(54) AAV PRODUCTION USING SUSPENSION ADAPTED CELLS

(71) Applicant: University of Florida Research Foundation, Incorporated, Gainesville, FL (US)

(72) Inventors: Nathalie Clement, Gainesville, FL (US); Barry John Byrne, Gainesville, FL (US); Laura A. Small, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 508 days.

(21) Appl. No.: 16/065,546

(22) PCT Filed: Dec. 23, 2016

(86) PCT No.: PCT/US2016/068562
§ 371 (c)(1),
(2) Date: Jun. 22, 2018

(87) PCT Pub. No.: WO2017/112948
PCT Pub. Date: Jun. 29, 2017

(65) Prior Publication Data
US 2020/0224173 A1 Jul. 16, 2020

Related U.S. Application Data

(60) Provisional application No. 62/387,553, filed on Dec. 24, 2015, provisional application No. 62/432,204, filed on Dec. 9, 2016.

(51) Int. Cl.
*C12N 7/00* (2006.01)
*C12N 15/86* (2006.01)

(52) U.S. Cl.
CPC ............. *C12N 7/00* (2013.01); *C12N 15/86* (2013.01); *C12N 2710/16644* (2013.01); *C12N 2750/14151* (2013.01)

(58) Field of Classification Search
None
See application file for complete search history.

(56) References Cited

U.S. PATENT DOCUMENTS 6,416,992 B1 * 7/2002 Mejza .................... C12N 7/00
435/235.1
6,593,123 B1 * 7/2003 Wright .................... C12N 7/00
210/656

(Continued)

FOREIGN PATENT DOCUMENTS

WO WO 2015/031686 A1 3/2015

OTHER PUBLICATIONS

International Search Report and Written Opinion for Application No. PCT/US2016/068562 dated Mar. 31, 2017.

(Continued)

*Primary Examiner* — M Franco G Salvoza
(74) *Attorney, Agent, or Firm* — Wolf, Greenfield & Sacks, P.C.

(57) ABSTRACT

Provided herein are methods of improving rAAV production in cells, the method comprising increasing the salt concentration in the media in which the cells are infected or transfected, cultured, or in which they produce AAV. Aspects of the disclosure relate to improved methods of rAAV production by co-infecting suspension adapted cells (e.g., suspension adapted HEK293 cells) with viruses that encode one or more AAV components for producing rAAV particles within the suspension adapted cells.

14 Claims, 25 Drawing Sheets

(56) References Cited

U.S. PATENT DOCUMENTS

| | | | |
|---|---|---|---|
| 6,989,264 B2* | 1/2006 | Atkinson | A61K 48/0091 |
| | | | 435/239 |
| 2005/0002908 A1* | 1/2005 | Horer | C12N 15/86 |
| | | | 424/93.2 |
| 2009/0275107 A1* | 11/2009 | Lock | C07K 14/005 |
| | | | 435/239 |
| 2014/0242671 A1 | 8/2014 | Grieger et al. | |
| 2015/0024467 A1 | 1/2015 | Sheldon et al. | |

OTHER PUBLICATIONS

International Preliminary Report on Patentability for Application No. PCT/US2016/068562 dated Jul. 5, 2018.

* cited by examiner

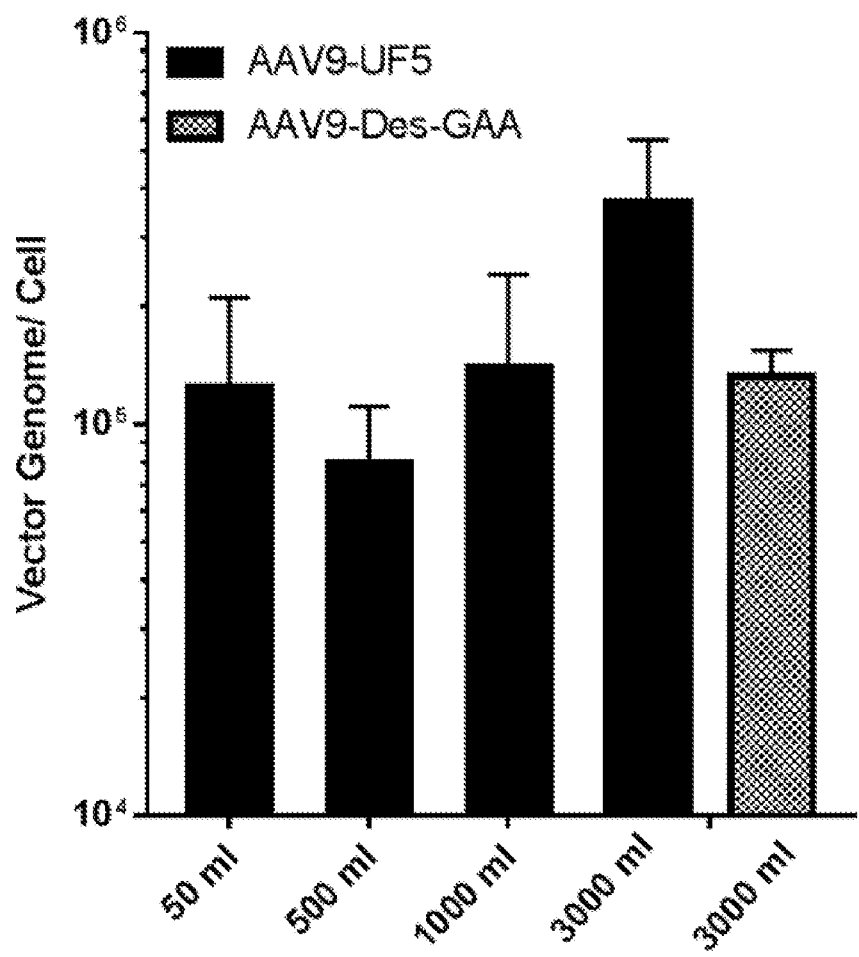

| Cell line | Media | Production Method | % Full |
|---|---|---|---|
| HEK293 | DMEM+5% FBS | TFX | 16.6 ± 5.36 |
| | DMEM+5% FBS | HSV | 20.81 ± 8.75 |
| | DMEM+5% FBS +NaCl | HSV | 24.2 ± 4.78 |
| Expi293F | Expi293F + NaCl | HSV | 32.08 ± 7.00 |

# AAV PRODUCTION USING SUSPENSION ADAPTED CELLS

RELATED APPLICATIONS

This application is a national stage filing under 35 U.S.C. 371 of International Patent Application Serial No. PCT/US2016/068562, filed Dec. 23, 2016, which claims the benefit of U.S. Provisional Application No. 62/387,553, filed on Dec. 24, 2015, and U.S. Provisional Application 62/432,204, filed on Dec. 9, 2016, the entire disclosures of each of which are incorporated in their entirety by reference herein.

GOVERNMENT SUPPORT

The invention was made with government support W81XWH-13-1-0283 awarded by US Department of Defense under Army/MRMC. The government has certain rights in the invention.

BACKGROUND

Adeno-associated virus (AAV) vectors are commonly used for research and also for gene therapy applications, including several in clinical development.

Methods and compositions for producing recombinant adeno-associated virus (rAAV) in large scale are useful for research, pre-clinical, and clinical applications. Therefore, there is a need for techniques to improve the productivity and yield of large scale rAAV particles.

SUMMARY AND DETAILED DESCRIPTION

Recombinant AAV particle production can involve (1) culturing cells, (2) introducing AAV genes and any genes desired to be packaged in rAAV particles to the cells, and (3) allowing the cells to produce or package rAAV. The present disclosure provides methods of producing rAAV that result in improved productivity and yield. The present disclosure is based, at least in part, on the recognition that the concentration of salt in the media in which the rAAV particle producing cells are infected or transfected with genes (infection or transfection media), or in which rAAV particles are produced (producer media), greatly influences the productivity of rAAV particles. It should be understood that it is not general practice to adjust or supplement infection or transfection media, or producer media with salt. The methods involving supplementing transfection or infection media, and/or producer media with salt are not only applicable to different AAV serotypes and transgenes to be packaged into rAAV particles, but also compatible with process regulations required for manufacturing of clinical compounds.

Accordingly, provided herein is a method of improving rAAV production in cells, the method comprising supplementing with salt either the media in which the cells are infected or transfected to introduce AAV rep and cap genes and/or genes of interest (transfection or infection media), or the media in which cells produce rAAV particles (producer media). In some embodiments, salt is supplemented in both transfection or infection media, and producer media.

In some embodiments, supplementing with salt is carried out before, at or after the time of transfection or infection in the infection media.

In some embodiments, the producer media is the same as the transfection or infection media. In some embodiments, culture media, such as media in which cells are cultured prior to being transfected or infected, is the same as the transfection or infection media.

In some embodiments, any one of the methods disclosed herein further comprises diluting or changing the producer media such that the concentration of salt is decreased. In some embodiments, the diluting or changing the producer media 0.5-8 h after supplementing the producer media or the transfection or infection media with salt.

In some embodiments, the salt is an inorganic salt. In some embodiments, the salt is an alkali halide (e.g., NaCl). In some embodiments, the salt is one or more of the following: aluminum chloride, magnesium chloride, lithium selenide, sodium carbonate, lithium chloride, sodium hydrogen phosphate, sodium metasilicate, strontium hydroxide, trisodium phosphate, potassium fluoride, magnesium sulfate, calcium chloride, sodium sulfate, aluminum sulfate, sodium tetraborate, magnesium sulfate, magnesium bromide, rubidium aluminum sulfate, barium hydroxide, potassium aluminum sulfate, magnesium nitrate, sodium hydrogen phosphate, nickel sulfate, zinc sulfate, beryllium sulfate, lithium nitrate, strontium chloride, zinc nitrate, sodium pyrophosphate, calcium bromide, copper sulfate, copper nitrate, aluminum nitrate, sodium tetraborate, silver fluoride, calcium iodide, lithium bromide, lithium iodide, strontium bromide, calcium nitrate, strontium iodide, sodium bromide, and strontium nitrate.

In some embodiments, a known volume of known concentration of supplemented salt solution is added to a media to result in a known concentration of supplemented salt in the media. In some embodiments, the concentration of supplemented salt in the media is between 5 mM and 200 mM. In some embodiments, the concentration of supplemented salt in the media is between 30 mM and 150 mM. In some embodiments, the concentration of supplemented salt in the media is between 60 mM and 90 mM. In some embodiments, the concentration of supplemented salt in the media is between 200 mM and 250 mM. In some embodiments, the concentration of supplemented salt in the media is between 250 mM and 300 mM. In some embodiments, the concentration of supplemented salt in the media is between 300 mM and 400 mM. In some embodiments, the concentration of supplemented salt in the media is between 400 mM and 500 mM. In some embodiments, the concentration of supplemented salt in the media is between 500 mM and 1 M. However, it should be appreciated that other concentrations of supplemented salt may be used in one or more media. In some embodiments, the media already had an initial salt concentration (e.g., of the same salt and/or of a different salt) which may be known or unknown. In such instances, the concentration of the supplemented salt in the media is an additional salt content of the media relative to the initial salt content prior to the addition of the supplemented salt. In some embodiments, the supplemented salt is the only salt in the media and the concentration of supplemented salt in the media is the actual salt concentration of the media.

In some embodiments, the concentration of salt is supplemented such that the total concentration of salt in a supplemented media is between 125 and 250 mM. In some embodiments, the concentration of salt is supplemented such that the total concentration of salt in a supplemented media is between 130 and 200 mM. In some embodiments, the concentration of salt in a supplemented media is supplemented such that the total concentration of salt is between 135 and 180 mM. In some embodiments, the concentration of salt in a supplemented media is supplemented such that the total concentration of salt is between 200 and 250 mM. In some embodiments, the concentration of salt in a supplemented media is supplemented such that the total concentration of salt is between 200 and 300 mM. In some embodiments, the concentration of salt in a supplemented media is supplemented such that the total concentration of salt is between 300 and 400 mM. In some embodiments, the concentration of salt in a supplemented media is supplemented such that the total concentration of salt is between 400 and 500 mM. In some embodiments, the concentration of salt in a supplemented media is supplemented such that the total concentration of salt is between 500 mM and 1 M.

It should be appreciated that the concentration of supplemented salt and/or the total concentration of salt can be the concentration of a single salt or a combined concentration of two or more salts (e.g., 2-5, 5-10, or more different salts).

In some embodiments, the AAV rep and cap genes and/or genes of interest are introduced to the cells by transfection of one or more plasmid vectors. In some embodiments, the AAV rep and cap genes and/or genes of interest are introduced to the cells by infection by one or more viral vectors. In some embodiments, the one or more viral vectors are one or more rHSV vectors.

In some embodiments, cells used to produce rAAV particles are cultured in adherent format or suspension format. In some embodiments, the cells are cultured on microcarriers that are in suspension.

In some embodiments, the one or more rHSV vectors comprise a first rHSV encoding a gene of interest flanked by AAV ITRs, and, a second rHSV encoding AAV rep and cap genes. In some embodiments, the AAV ITRs are AAV-2 ITRs. In some embodiments, the AAV ITRs are from AAV-1, AAV-3, AAV-4, AAV-5, AAV-6, AAV-7, AAV-8, AAV-9, AAV-10, AAV-11, AAV-12 or other AAV serotype. In some embodiments, the AAV cap gene is an AAV-9, AAV-2 or AAV-5 cap gene.

In some embodiments, the rep and cap genes are operably linked to a promoter.

In some embodiments, cells used to produce rAAV particles are mammalian or insect cells. In some embodiments of any one of the methods disclosed herein, the mammalian cells used to produce rAAV particles are HEK293 cells, BHK cells, HeLa cells, or any other suitable cells.

In some aspects, this disclosure is also based on the finding that supplementing cell cultures with salt during production of rAAV for both cells cultured in adherent form or in suspension reduces degradation of rAAV particles and contamination by cellular proteins and HSV proteins compared to when salt is not supplemented. It was also found that rAAV prepared in cells that are infected using viral vectors (e.g., HSV) to introduce necessary AAV proteins have less degradation of rAAV particles and less contamination by cellular proteins and HSV proteins compared to cells that are transfected. Accordingly, this disclosure provides compositions and methods for improving the quality of rAAV preparations. In some embodiments, quality of rAAV preparations refers to contamination by either proteins from the cells used to prepare rAAV (e.g., HEK293 cells), or a virus used to infect the cells used to prepare rAAV (e.g., HSV to introduce rep or cap protein to the cells). In some embodiments, quality of rAAV preparations refers to degradation of the rAAV particles in the preparation. Degradation of rAAV particles can be assessed by traditional methods known in the art, for example by SDS gel electrophoresis (see FIG. 16A). In some embodiments, a method of improving the quality of rAAV preparations comprises supplementing with salt either media in which the cells are infected or transfected to introduce AAV rep and cap genes and/or genes of interest (transfection or infection media), or the media in which cells produce rAAV particles (producer media). In some embodiments of any of the methods to improve the quality of rAAV preparations as provided herein, the cells used for preparing rAAV particles are adherent and supplemented with salt. In some embodiments of any of the methods to improve the quality of rAAV preparations as provided herein, the cells used for preparing rAAV particles are in suspension culture and supplemented with salt.

The present disclosure also provides a scalable rAAV production method that utilizes suspension-adapted cells (e.g., suspension-adapted HEK293 cells) combined with a serum and animal-component free media that enables production of high titer, high potency and high quality rAAV vector preparation in a GLP/GMP-compatible overall process.

Recombinant adeno-associated viral vectors (rAAV) have become a powerful research and clinical tool due to their ability to provide in vivo long-term gene expression[1]. As the uses for rAAV grow, so does the need for large-scale manufacturing methods capable of generating high titers of high quality vector, to not only meet the needs for preclinical studies and clinical trials, but the strict quality standards established by the FDA for a gene therapy drug in compliance with current Good Manufacturing Practice (cGMP), CFR21). Yet the widespread full scale clinical use of rAAV, in view of commercialization, has long been hampered by manufacturing limitations that have appeared as one of the greatest challenge undermining the production of large quantities of rAAV needed for clinical trials[2].

Currently, there are 3 main methods utilized for rAAV production: transfection, producer cell lines, and viral infection[2]. A majority of transfection protocols rely on double or triple plasmid transfection of adherent HEK293 cells and are considered not scalable due to the linear increase of flat surface for cell culture. However, suspension culture is a very scalable cell culture platform for rAAV manufacturing. Recent alternatives to HEK293 transfection on flat stocks utilized suspension-adapted HEK293 cells combined with a transfection process[3-5]. Using PEI transfection of suspension adapted HEK293 cells, production of greater than $1 \times 10^{14}$ vector genomes per liter of cell crude harvest, resulting in approximately $3 \times 10^{13}$ purified rAAV vector[6] was reported. The method was shown adaptable to multiple rAAV serotypes in a fully scalable method. Alternatively, stable cell line production relies on the introduction of and selection of cells containing either the AAV rep and cap genes or the rAAV genome of interest[7, 8]. The main advantage of this method is the increased probability that each cell may result in a rAAV production center, especially when combined with a high transfection or infection efficiency. Detailed publications are somewhat lacking and the true potential of this method remains to be demonstrated at commercial scale. It is believed that the method is capable of generating high titer AAV preparations with a possible reduction of the amount of empty capsids. Among some of the potential issues with cell line derivatives is vector or insert integration loss during prolonged passaging of the cells and the potential for residual adenovirus particles in rAAV products[9, 10], in cases where Adenovirus is used. Last, methods based on viral infection for rAAV production have been developed utilizing either Baculovirus or Herpes Simplex Virus type 1 (HSV). The concept of both methods is relatively similar with rAAV production triggered in the host cells, insect cells or mammalian cells, respectively, upon co-infection with 2 or more recombinant viruses carrying the various AAV regions, such AAV genome, AAV Rep and AAV Cap. In both systems, the shuttle virus, Baculovirus or HSV, provides the helper functions required for rAAV replication and packaging[2,11]. The main advantage of the infection-based production platforms is the ability to use suspension cultures to streamline the scalability towards hundreds of liters of production harvests. In some embodiments, methods provided herein may be used in conjunction with any one of these three methods of producing rAAV—transfection, producer cell lines, and viral infection.

Previously, an optimized protocol for high yield production of rAAV9 stocks at high titers using HEK293 flat stocks[12] was reported. This protocol generated high quality material at approximately 5- to 10-fold increase in AAV yield when compared to transfection-made material, and utilized media containing 5% fetal bovine serum (FBS). Production of AAV in a suspension format has already been described using baby hamster kidney cells (BHK21) demonstrating the feasibility of this platform for scale-up. However, the published production protocol also reported the use of media containing 10% fetal bovine serum (FBS) or required media change to serum free 4 to 6 hours following rHSV infection, both resulting in overall yields that were below those reported in the adherent 293 platform[12,13]. A recent study reports rAAV production utilizing the rHSV BHK suspension platform in serum-free media, but vector yields and detailed description of the manufacturing methods are not described[14,15]. In some embodiments, methods provided herein may be used in conjunction with any one of these three methods of producing rAAV.

Accordingly, in some embodiments a method of producing rAAV comprises co-infecting adherent or suspension-adapted cells (e.g., HEK293 cells) with: a first rHSV encoding a gene of interest flanked by AAV ITRs, and, a second rHSV encoding AAV rep and cap genes. In some embodiments, the method further comprises isolating rAAV from the co-infected adherent or suspension-adapted cells (e.g., HEK293 cells) and/or from media in which the co-infected suspension-adapted cells (e.g., HEK293 cells) produced rAAV.

In some embodiments of any of the method disclosed herein, suspension-adapted HEK293 cells are derived from adherent HEK293 cells. In some embodiments, suspension-adapted HEK293 cells are obtained from a commercial source.

In some embodiments, suspension-adapted cells are cultured in a shaker flask, a spinner flask, a cellbag, or a bioreactor.

In some embodiments, one or more of the AAV rep or cap genes are delivered to the suspension-adapted cells using more than one second rHSV.

In some embodiments of a method to use adherent or suspension-adapted cells (e.g., HEK293 cells) to produce rAAV particles, the AAV ITRs are AAV-2 ITRs. In some embodiments, the AAV ITRs are from AAV-1, AAV-3, AAV-4, AAV-5, AAV-6, AAV-7, AAV-8, AAV-9, AAV-10, AAV-11, AAV-12 or other AAV serotype. In some embodiments, the AAV cap gene is an AAV-9, AAV-2 or AAV-5 cap gene. In some embodiments, the rep and cap genes are operably linked to a promoter. In some embodiments, the gene of interest is operably linked to a promoter. In some embodiments, a promoter is a native promoter.

In some embodiments of a method to use adherent or suspension-adapted cells (e.g., HEK293) cells to produce rAAV particles, the gene of interest is operably linked to a promoter. In some embodiments, the gene of interest encodes a therapeutic protein. In some embodiments, the therapeutic protein is therapeutic for lysosomal storage disease. In some embodiments, the therapeutic protein is therapeutic for lysosomal storage disease. In some embodiments, the therapeutic protein is therapeutic for a muscular disability, myopathy or cardiomyopathy.

Aspects of the disclosure relate to improved methods of AAV production using suspension adapted cells (e.g., suspension adapted HEK293 cells). In some embodiments, AAV can be produced by co-infecting host cells with recombinant viruses (e.g., recombinant HSV) that deliver a recombinant AAV genome (e.g., a gene of interest flanked by AAV inverted terminal repeat sequences), and AAV Rep and Cap genes. The expressed Rep and Cap proteins promote replication and encapsidation of the AAV genome inside the host cell, resulting in the production of rAAV particles comprising the rAAV genome within a particle of AAV capsid proteins. In some embodiments, the host cell that is used is a suspension adapted host cell (e.g., a suspension adapted HEK293 cell line).

AAV (e.g., rAAV) used for research and clinical applications are commonly produced on Human Embryonic Kidney cells (HEK293) by transfection or infection using cells that are grown on an adherent flat platform (e.g., culture vessels like Corning® 225 or Corning CellSTACK® flasks). According to aspects of the application, the adherent platform can be a significant scale-up limiting factor. As described herein, in some embodiments a production protocol based on coinfection of a suspension-adapted HEK293 cell line provides significantly improved yields relative to other platforms, for example adherent HEK293, or suspension-adapted Baby Hamster Kidney (BHK) cells.

In some embodiments, suspension-adapted HEK293 cells can be obtained from adherent HEK293 cells. In some embodiments, suspension-adapted HEK293 cells can be obtained from a commercial source.

In some embodiments, suspension-adapted HEK293 are highly permissive to HSV infection, and can be used for the production of infectious AAV particles using HSV infection protocols. In some embodiments, protocols for large scale AAV manufacturing can be based on using suspension-adapted HEK293, for example to generate high yields of potent vector particles. The production of high titer highly potent rAAV preparations provides significant advantages over currently available protocols and supports large scale clinical research that benefits patients worldwide.

In some embodiments, a unique advantage of the HEK293 suspension platform is the high quality of the virus generated. The potency of the virus generated from HEK293 is significantly higher than when produced by transfection, or by infection of suspension BHK cells. Other methodologies have failed to provide any advantages related to vector potency. In contrast the present suspension format allows for very large-scale, high titer, and high potency, viral (e.g., rAAV) manufacturing. This allows for comprehensive and exhaustive pre-clinical and clinical studies. This can have a significant impact on the many genetic diseases in need of efficient therapeutic protocols and for which none currently exist. In some embodiments, the present suspension format also allows for bulk manufacturing (e.g., of rAAV) in short time periods using low amounts of human manipulation, thereby reducing the cost of manufacturing and the resulting cost of production (e.g., of a therapeutic rAAV).

FIG. 1 illustrates a non-limiting embodiment of a viral co-infection protocol in which two different HSV viral vectors are used to deliver a recombinant AAV genome comprising a gene of interest flanked by AAV inverted terminal repeat sequences (ITRs). The HSV vectors are used to co-infect suspension-adapted HEK293 cells. rAAV particles are then obtained from the co-infected cells.

In some embodiments, two or more recombinant rHSV-1 viruses are used to simultaneously co-infect the suspension cells (e.g., the suspension adapted HEK293 cells) with all of the components necessary for rAAV production. HSV-1 can fully support AAV replication and packaging (Knipe, 1989; Advances in Virus Research 37:85-123, Buller, J Virol. 1981 October; 40(1):241-7, Mishra and Rose, Virology. 1990 December; 179(2):632-9, Weindler et al., J Virol. 1991 May; 65(5):2476-83) in other production formats and was found to be effective in suspension-adapted HEK293 cells too. In some embodiments, certain HSV-1 genes required to replicate and package AAV (e.g., UL5, ULB, UL52 and UL29— Weindler et al., J Virol. 1991 May; 65(5):2476-83) are maintained within one or more rHSV used for co-infection of suspension-adapted HEK293 cells. These genes encode components of the HSV-1 core replication machinery and by themselves form nuclear prereplication centers that develop into mature replication foci (Weindler et al., J Virol. 1991 May; 65(5):2476-83, Knipe, D. M., Advances in Virus Research 37:85-123). In the context of suspension-adapted HEK293 cells, recombinant HSV-1 viruses are also used to supply the helper functions needed for rAAV production.

In some embodiments, two different forms of rHSV are used, each containing a different gene cassette. In addition to supplying the necessary helper functions, each of these rHSV viruses is engineered to deliver different AAV (and other) genes to the suspension cells (e.g., HEK293 cells) upon infection. In some embodiments, a first recombinant HSV (e.g., HSV1 in FIG. 1) contains transgene nucleic acid, for example having sequences encoding a gene(s) of interest (GOI), along with promoter elements necessary for expression of the gene. Generally, the transgene nucleic acid is inserted between two AAV inverted terminal repeats (ITRs). In some embodiments, a second rHSV (e.g., HSV2 in FIG. 1) contains a gene cassette in which the rep and cap genes from AAV are inserted into the HSV genome. The rep genes are responsible for replication of the rAAV genome in host cells infected with AAV. The cap genes encode proteins that comprise the capsid of the rAAV produced by the infected cells.

In some embodiments, the first and second rHSV viruses are used to co-infect (e.g., simultaneously or at approximately the same time) the suspension cells (e.g., the suspension-adapted HEK293 cells).

In some embodiments, two or more rHSV viruses that are used for a simultaneous co-infection protocol to produce rAAV can be produced from HSV-1. In some embodiments, HSV used to produce rAAV can be of any variant (e.g., HSV-1 or HSV-2 or any other serotype or variant or mutant forms thereof).

In some embodiments, a second rHSV expressing AAV rep and cap genes in a mutant HSV-1 vector designated d27.1 (Rice and Knipe, J Virol., 1990; 64(4):1704-15) can be used and prepared as previously described (Conway et al., Gene Ther 1999; 6:986-993). As a result of the mutation, this vector does not produce ICP27. An advantage in the use of an ICP27 mutant for rAAV production is that host cell splicing of messenger RNA is known to be inhibited by ICP27 (Sandri-Goldin and Mendoza, Genes Dev. 1992 May; 6(5):848-63). ICP27 probably also effects the appropriate splicing of the AAV rep and cap messages. In some embodiments, this vector was used because it is replication defective and was expected to show reduced cytotoxicity compared with wild type (wt) HSV-1 in a non-permissive cell line.

The virus d27.1 displays several other features that make its use advantageous for the design of a helper virus for rAAV production. First, it expresses the early genes known to be required for rAAV production (Weindler et al., 1991, Rice and Knipe, 1990). In addition, d27.1 over-expresses ICP8, the single-stranded DNA binding protein that is the product of UL29, one of the HSV-1 genes essential for AAV replication and packaging (Weindler et al., J Virol. 1991 May; 65(5):2476-83, Rice and Knipe, 1990; 64(4):1704-15, McCarthy, et al., Am J Trop Med Hyg. 1989 December; 41(6):726-31; Clement et al., 2009). In some embodiment of the first HSV vector, the AAV rep and cap genes were expressed under control of the native AAV-2 rep and cap promoters. The p5 and p19 promoters of AAV-2 control expression of Rep 78 and 68 and Rep 52 and 40, respectively. The p40 promoter controls expression of VP1, VP2 and VP3. However, other promoters can be used.

In some embodiments, the first and second rHSV viruses can be produced using similar techniques (e.g., by homologous recombination into the HSV-1 tk gene).

In some embodiments, the AAV-2 ITR sequences are used to flank the gene of interest in the first rHSV virus. However, ITR sequences from other AAV serotypes can be used (e.g., from AAV-1, AAV-3, AAV-4, AAV-5, AAV-6, AAV-7, AAV-8, AAV-9, AAV-10, AAV-11, AAV-12 or other serotype). In some embodiments, one or more variant ITR sequences can be used.

In some embodiments, a gene of interest encodes an enzyme, hormone, antibody, receptor, ligand, or other protein. In some embodiments, a gene of interest encodes a therapeutically useful protein. In some embodiments, a gene of interest encodes a marker protein (e.g., GFP). In some embodiments, a gene of interest encodes an RNA, for example a regulatory RNA such as a siRNA or other regulatory RNA (e.g., an RNA can be therapeutically useful).

In some embodiments, a gene of interest (e.g., encoding a therapeutic agent) is operably linked to a promoter. In some embodiments, the therapeutic agent is a polypeptide, a peptide, an antibody or an antigen-binding fragment thereof, a ribozyme, a peptide-nucleic acid, an siRNA, an RNAi, an antisense oligonucleotide, or an antisense polynucleotide.

In some embodiments, a composition comprising an rAAV described herein can be used to treat a mammalian subject (e.g., a human). In some embodiments, the subject has cancer, diabetes, autoimmune disease, kidney disease, cardiovascular disease, pancreatic disease, intestinal disease, liver disease, neurological disease, neuromuscular disease, Bratten's disease, Alzheimer's disease, Huntington disease, Parkinson's disease, pulmonary disease, an α-1.alpha.-1 antitrypsin deficiency, neurological disability, neuromotor deficit, neuroskeletal impairment, ischemia, stroke, a lysosomal storage disease, Pompe disease, Duchenne Muscular Dystrophy, Friedreich's Ataxia, Canavan disease, Aromatic L-amino acid decarboxylase deficiency, Hemophilia A/B, or other disease, or any combination thereof.

In some embodiments, the AAV-2 (serotype 2) rep and cap genes are used for the second rHSV virus. However, one or more rep and/or cap genes form other AAV serotypes can be used (e.g., from AAV-1, AAV-3, AAV-4, AAV-5, AAV-6, AAV-7, AAV-8, AAV-9, AAV-10, AAV-11, AAV-12 or other serotype). In some embodiments, one or more variant cap genes can be used. In some embodiments, the rep and/or cap genes can be under the control of their natural AAV promoter. However, in some embodiments, they can be under the control of one or more constitutive or inducible promoters.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

Figure 1:
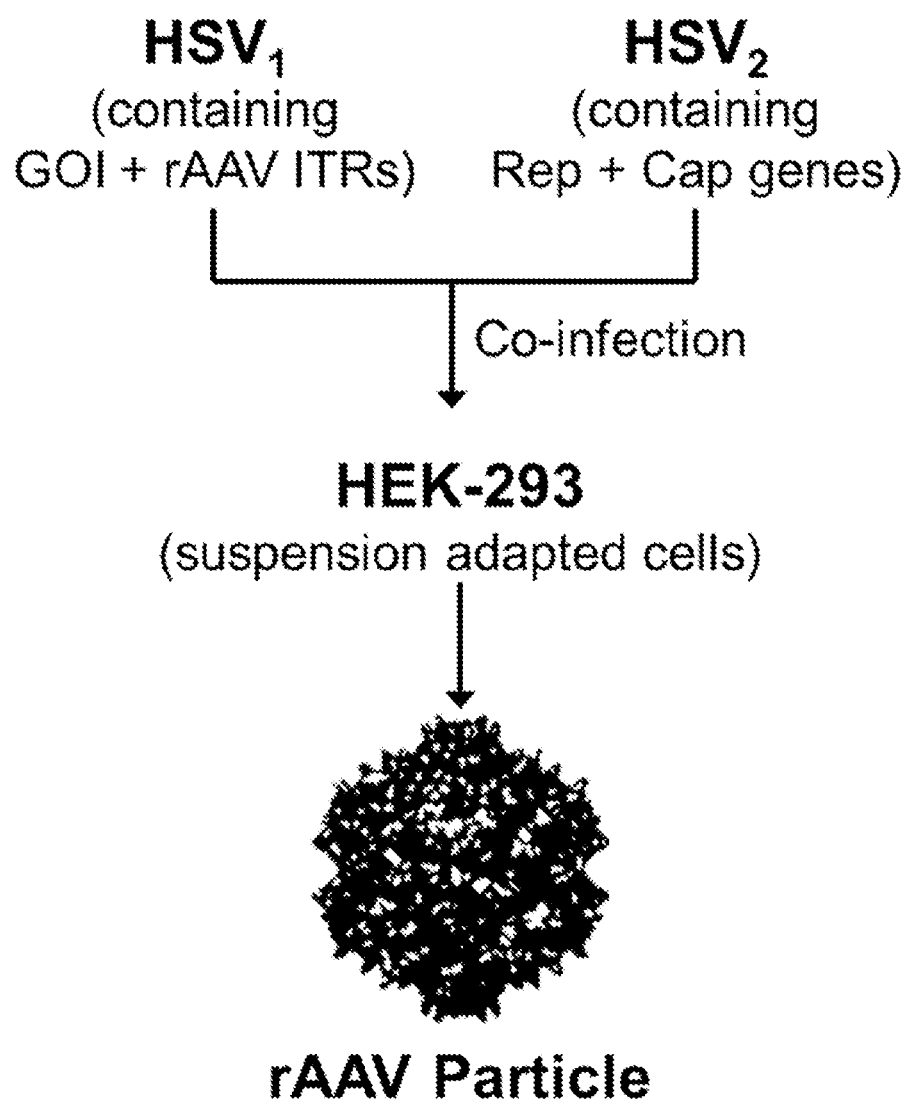
FIG. 1 shows one embodiment of how rAAV particles are produced as disclosed herein. Two HSVs, one containing a gene of interest (GOI) between rAAV ITRs, and the other containing rep and cap genes, are used to co-infect HEK-293 cells that are adapted for suspension culture. After cells package the gene of interest in rAAV particles, particles are harvested and purified.

Cell lines were co-infected with first and second rHSV as described herein. Approximately 1E8 cells were resuspended in fresh medium at 1E6 c/mL on the day of infection. Cells were harvested 48 hours post-infection by centrifugation and virus released by a series of 3 freeze/thaws in lysis buffer (Tris, NaCl, pH 8.5). Lysates were submitted to Benzonase digestion and clarified by centrifugation. Infectious titers were assayed by green cell assay (also known as transduction assay): C12 cells were infected by serial dilution of the AAV9-containing crude lysates and wtAd5. GFP-expressing cells were counted under the microscope after 48 hours and transducing titers calculated based on the dilution used. Total TU (transducing units) are shown in FIG. 1, showing the feasibility to use 293 cells freshly adapted in the laboratory as compared to commercially available cell lines.

Figure 3:
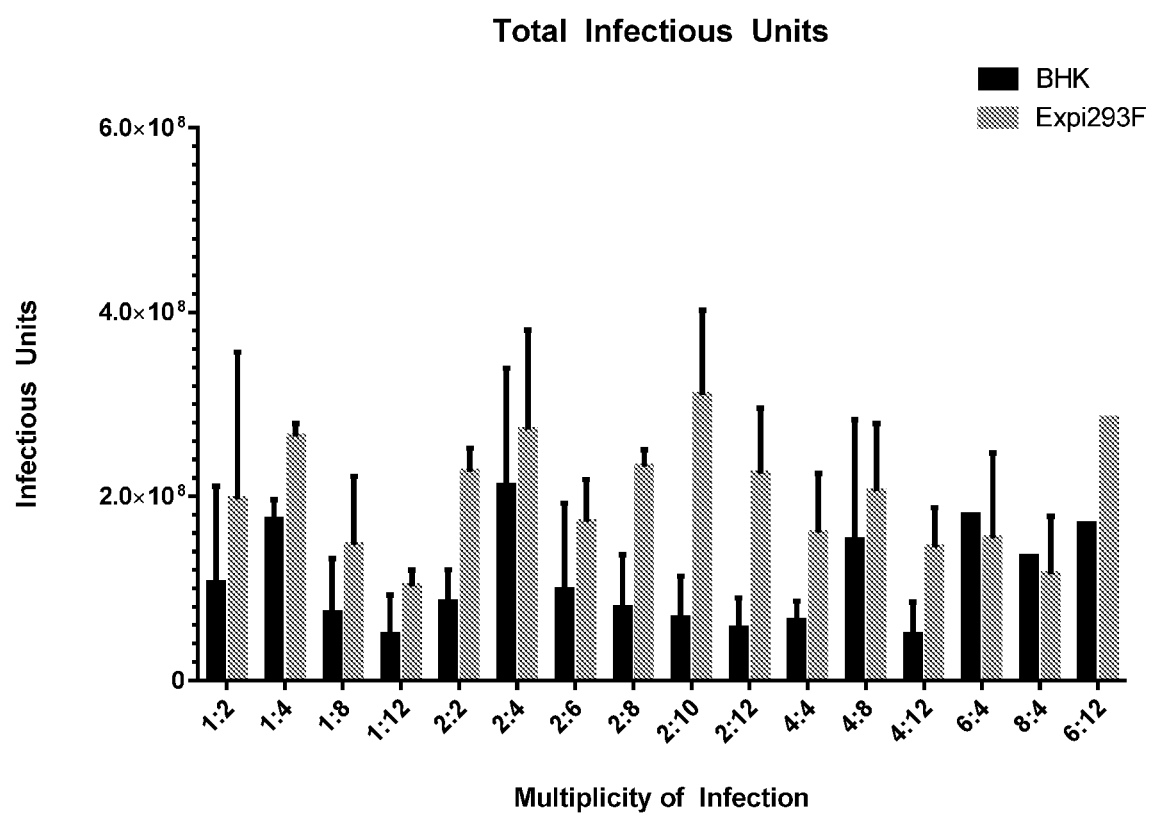

FIG. 3 shows effect of MOI on rAAV production in salt-optimized media. BHK and EXPI293F™ cells were co-infected with HSV-UF5 and HSV-AAV9 at various MOIs, and media was supplemented with NaCl so that the concentration of supplemented NaCl was 60 mM and 90 mM % for BHK and EXPI293F™ cells, respectively. There was no significant difference in rAAV production despite changes in HSV MOI when media was optimized for salt concentration.

Figure 4A:
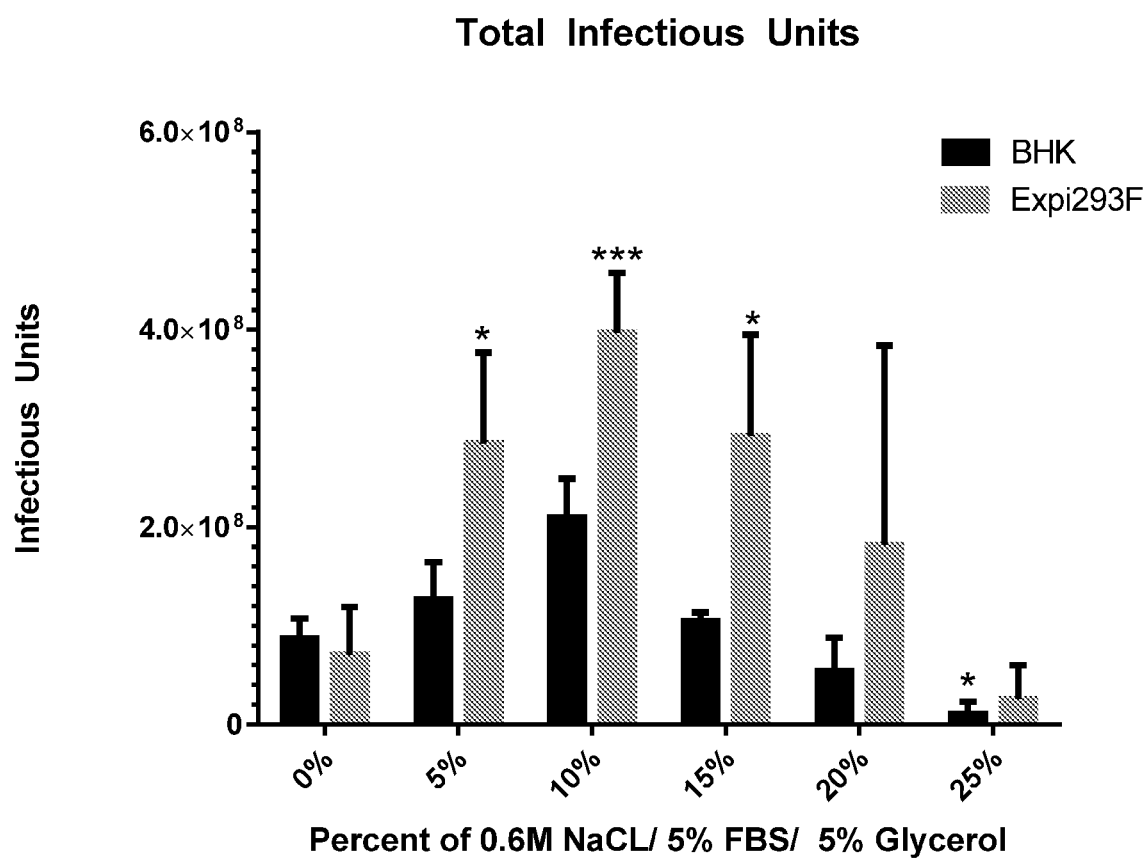
Figure 4B:
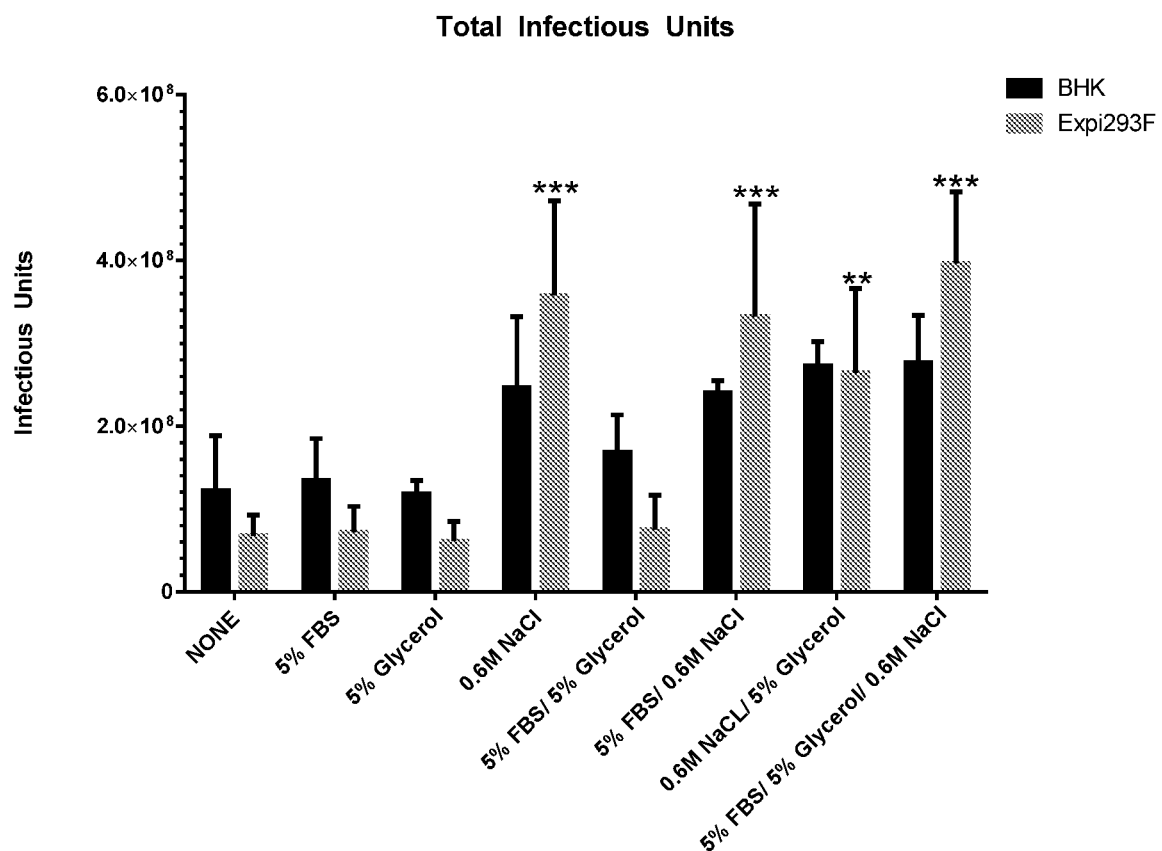
Figure 4C:
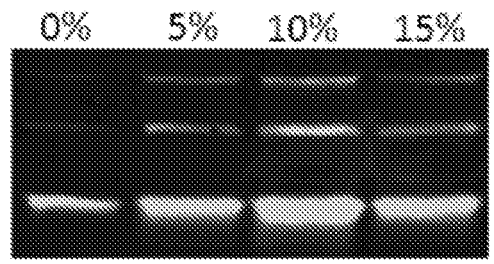
Figure 4D:
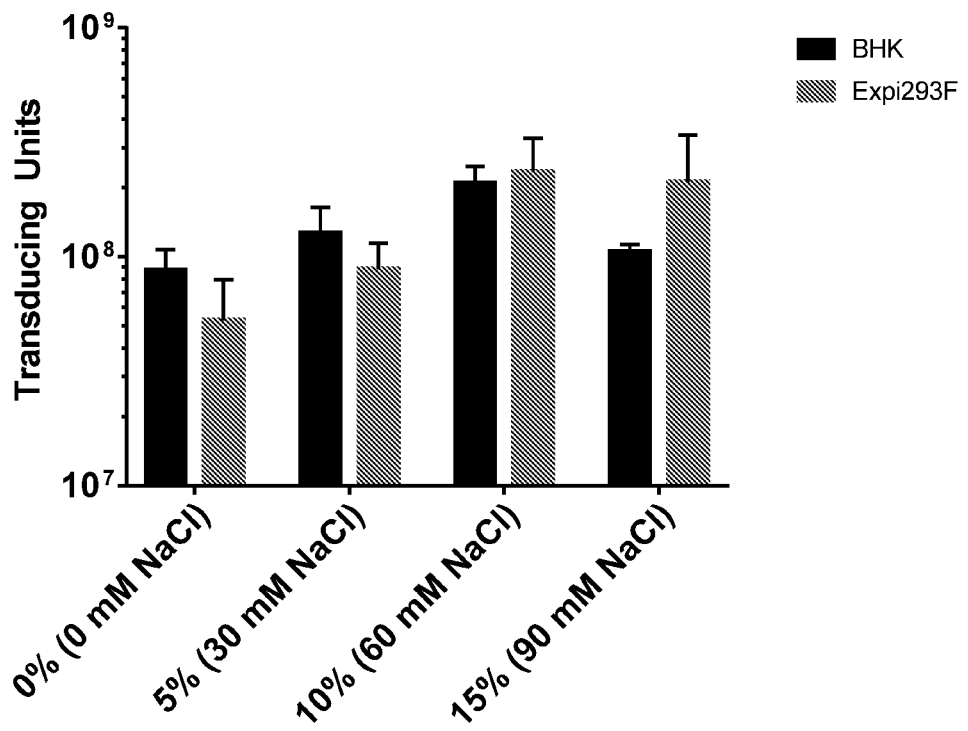
Figure 4D:
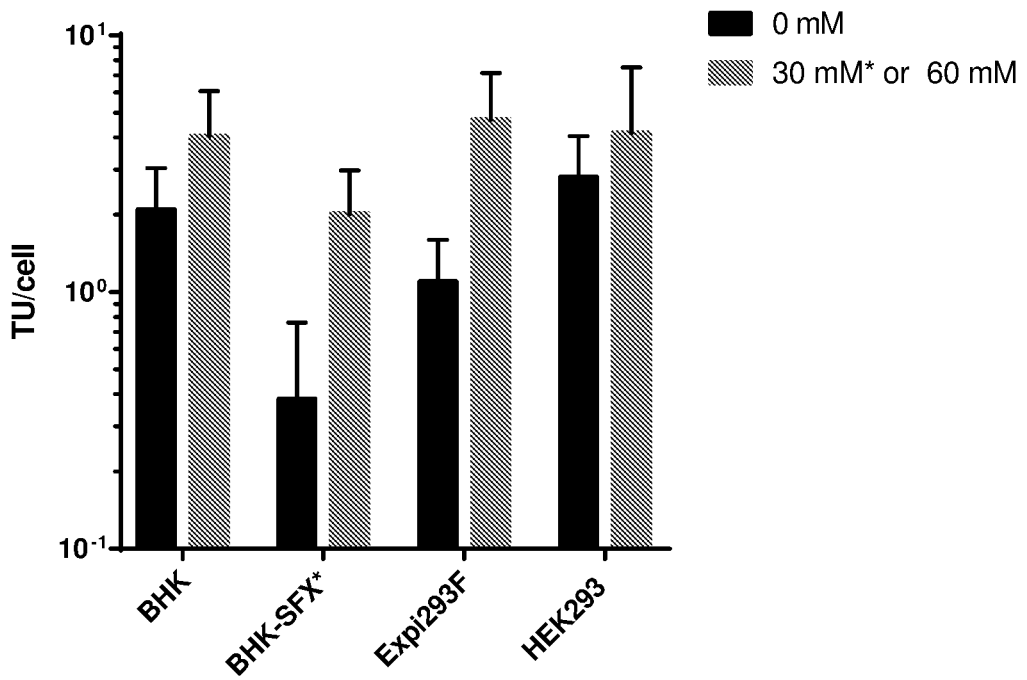
Figure 4E:
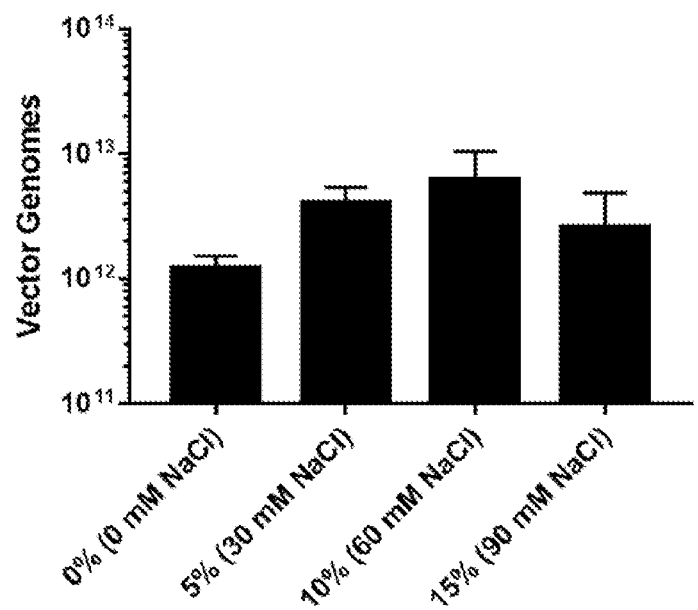
Figure 4F:
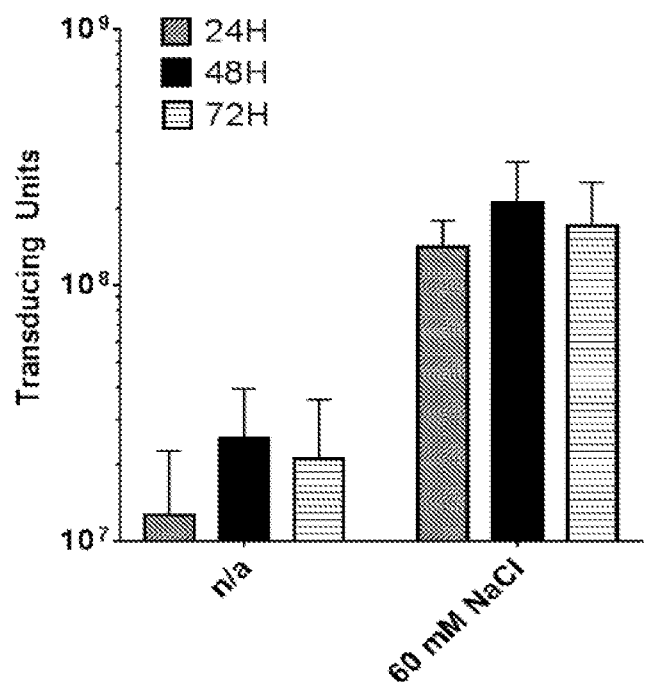
Figure 4G:
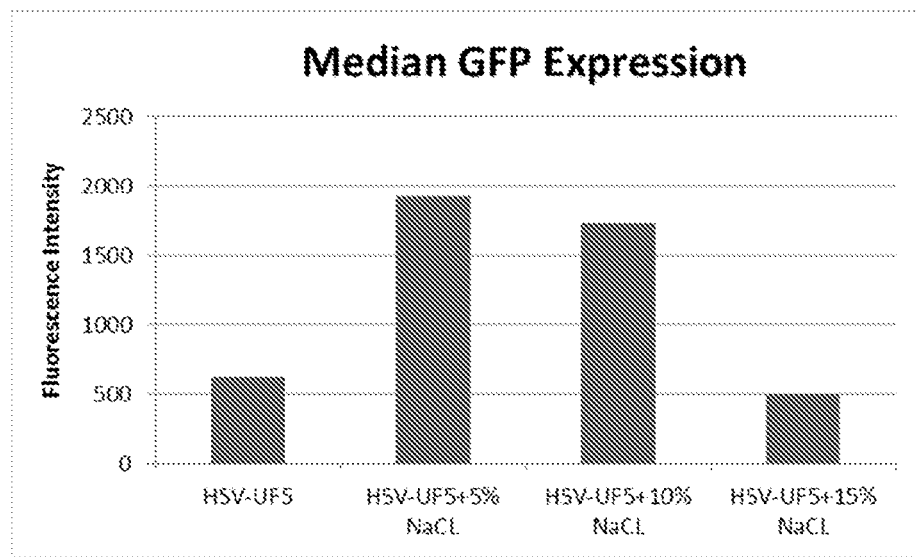
Figure 4H:
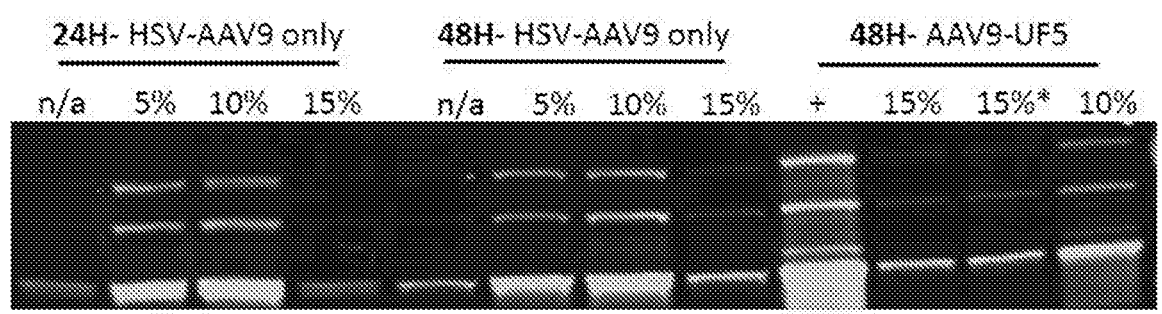

FIGS. 4A to 4H show that increased sodium chloride concentrations result in improved rAAV production following rHSV co-infection in two cell lines. FIG. 4A and FIG. 4B are graphs showing transducing units measured in cell lysates 48 hours post-infection in 50-ml working volume, with the media supplemented with increasing percentage of the complete HSV matrix (FIG. 4A) comprising of 5% FBS, 5% glycerol and 600 mM NaCl: 5% resulting in supplementation of 30 mM NaCL; 10% resulting in supplementation of 60 mM NaCl; 15% resulting in supplementation of 90 mM NaCL; 20% resulting in supplementation of 120 mM NaCL; 25% resulting in supplementation of 150 mM NaCL; or each component individually or in various combinations, respectively, at a final concentration of 15% of total media volume, corresponding to 90 mM NaCl supplementation for EXPI293™ and 60 mM for BHK (FIG. 4B). FIGS. 4C to 4E show increased rAAV9 capsid proteins, transducing units, and vector genomes measured in cell lysates 48 hours post-infection, in the presence 0-90 mM salt supplementation. FIG. 4F is a graph showing rAAV9-GFP particle production in the absence or presence of salt 24, 48, and 72 hours post-infection in EXPI293™. FIG. 4G and FIG. 4H show the impact of salt concentration on expression of GFP following HSV-transduction. EXPI293F™ cells were infected with HSV-UF5 (FIG. 4G) or HSV-AAV9 (FIG. 4H) at MOI of 2 and 4, respectively, either in EXPI293™ media alone or media supplemented with increasing amounts of 0.6M NaCl solution. For FIGS. 4A to 4H, *p<0.05, p<0.01, *p<0.001.

Figure 5A:
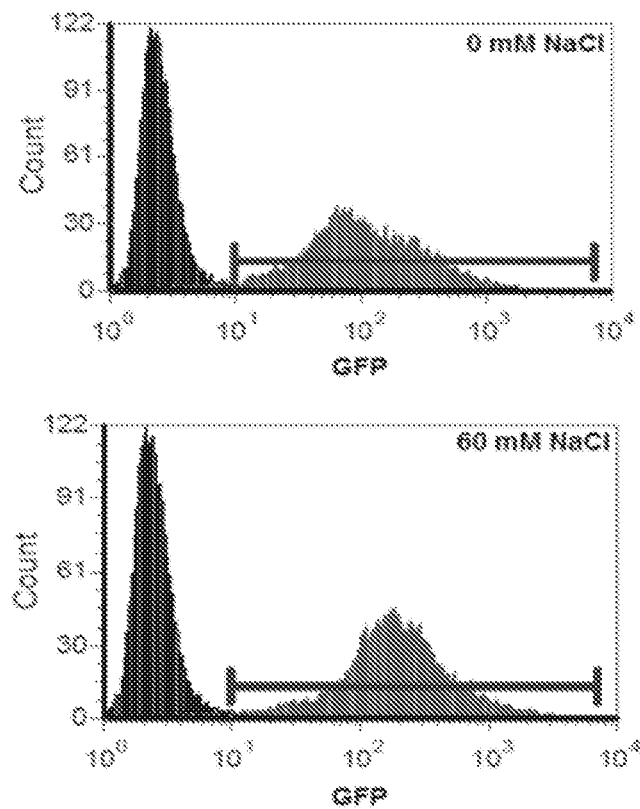
Figure 5B:
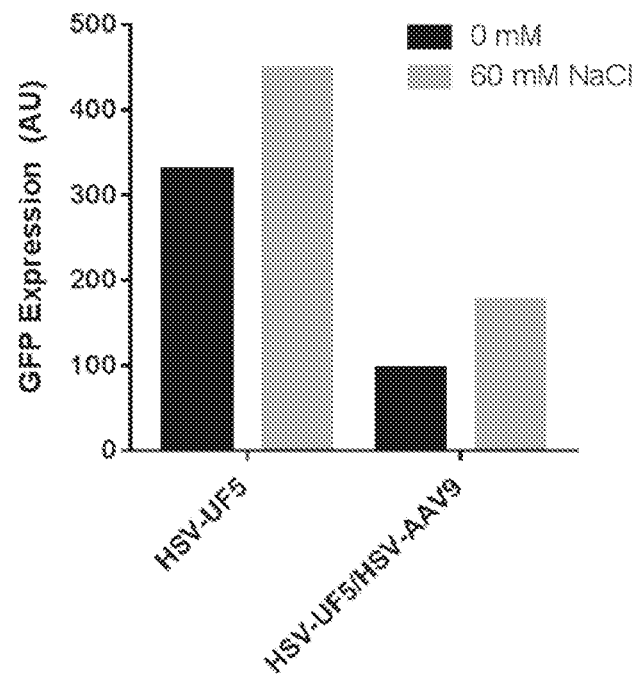
Figure 5C:
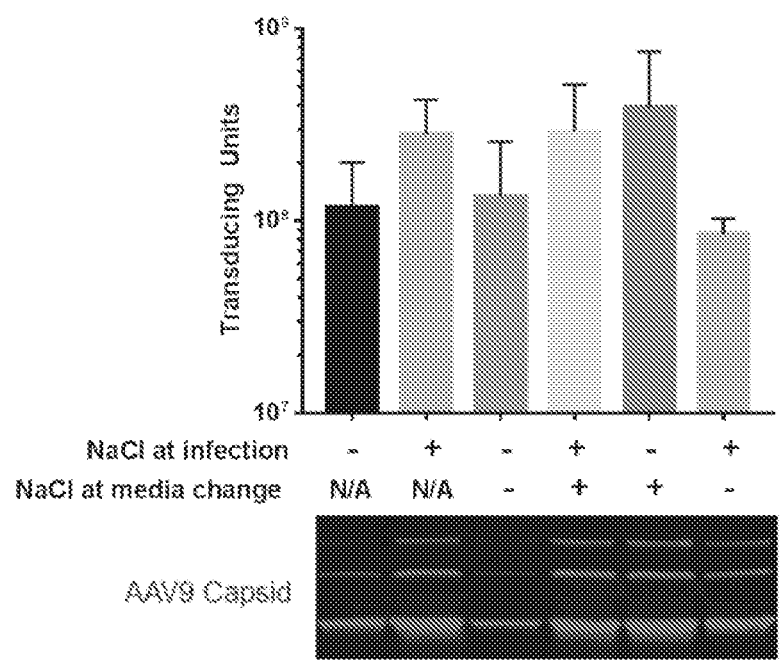
Figure 5D:
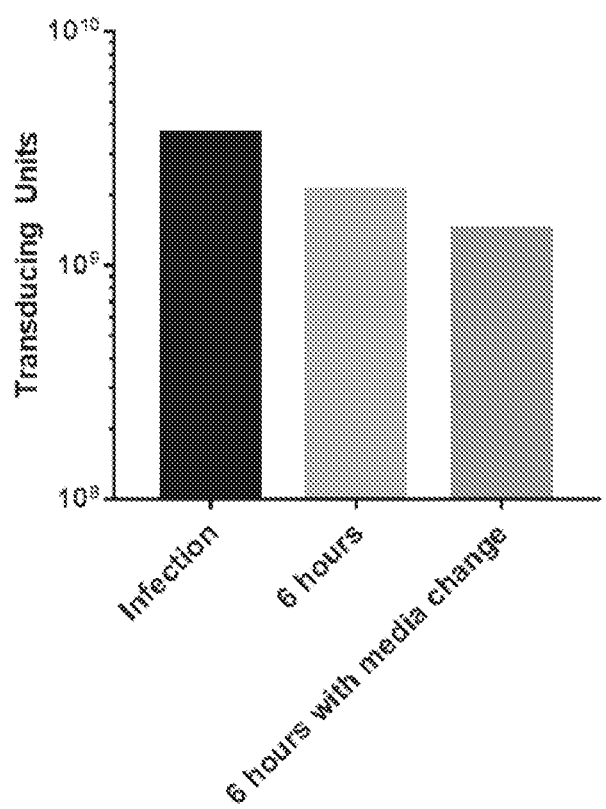
Figure 5E:
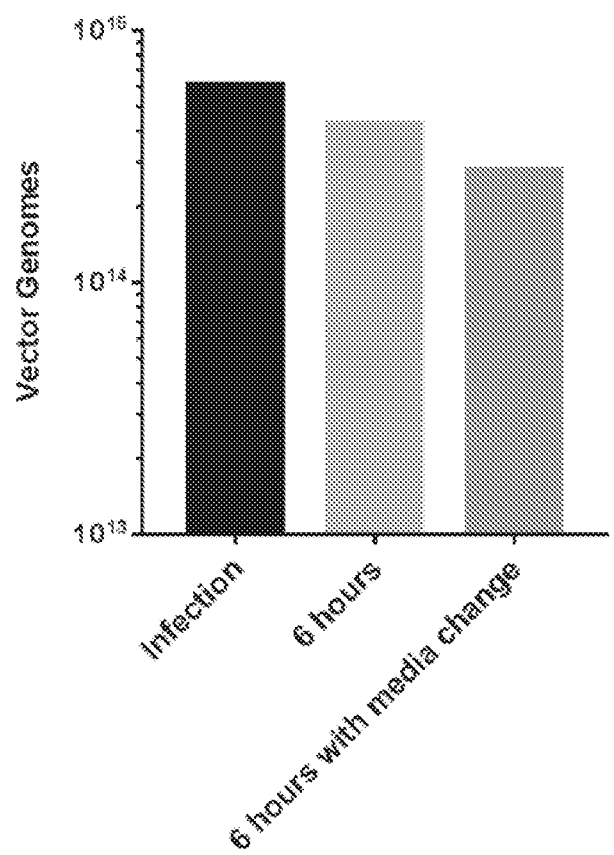

FIGS. 5A to 5E show increased sodium chloride is critical at 4-6 hours post-transduction for improved rAAV production. FIG. 5A and FIG. 5B show flow cytometry analysis of GFP-positive cells and GFP expression in EXPI293F™ cells transduced with rHSV-GFP in media alone or supplemented with 60 mM of sodium chloride, with an increased GFP expression in the presence of NaCl supplementation. FIG. 5C shows rAAV9-UF5 production in EXPI293F™ cells. EXPI293F™ cells were infected with rHSV-GFP and rHSV-AAV9 at an MOI ratio of 2:4, in EXPI293F™ media alone, or supplemented with 60 mM of sodium chloride. At 6 hours post-infection, flasks were either left alone (no media change), or switched to either EXPI293F™ media alone or supplemented with sodium chloride. Total rAAV9-UF5 production was evaluated in crude lysates 48 hours post-transduction by evaluating transducing units by green cell assay and rAAV9 capsid proteins by western blot. Optimal yields were obtained when NaCl was supplemented either at the time of the infection or 6 hours after co-infection occurred. FIG. 5D and FIG. 5E show that timing of salt introduction is important for rAAV production. Salt present during rHSV infection, added 6 hours post-transduction, or added in a complete media change at 6 hours post-transduction when tested using 3 L cultures is shown. rAAV production, as measured by total transducing units and vector genomes, was similar whether the salt supplementation was done at the time of infection or 6 hours post infection without media change.

Figure 6A:
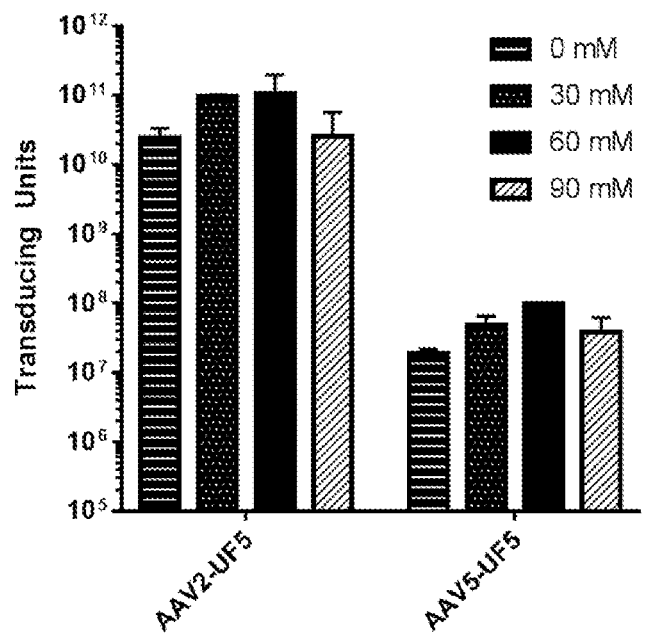
Figure 6B:
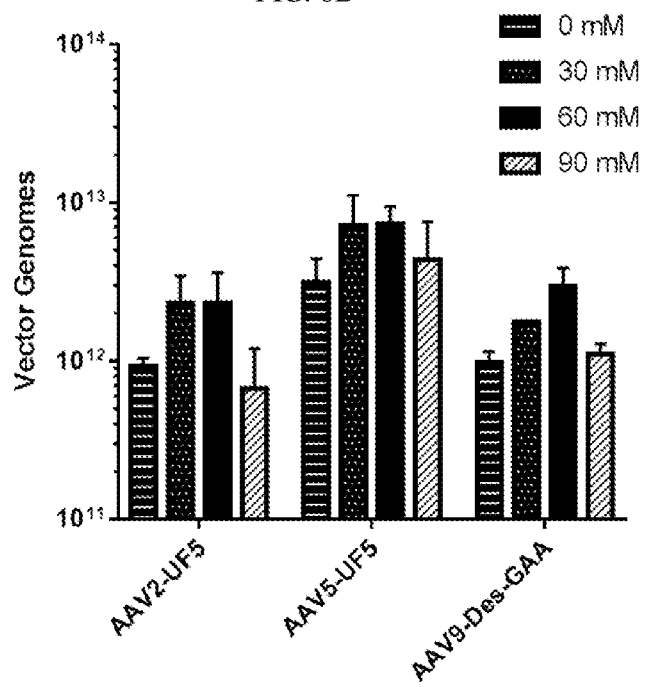
Figure 6C:
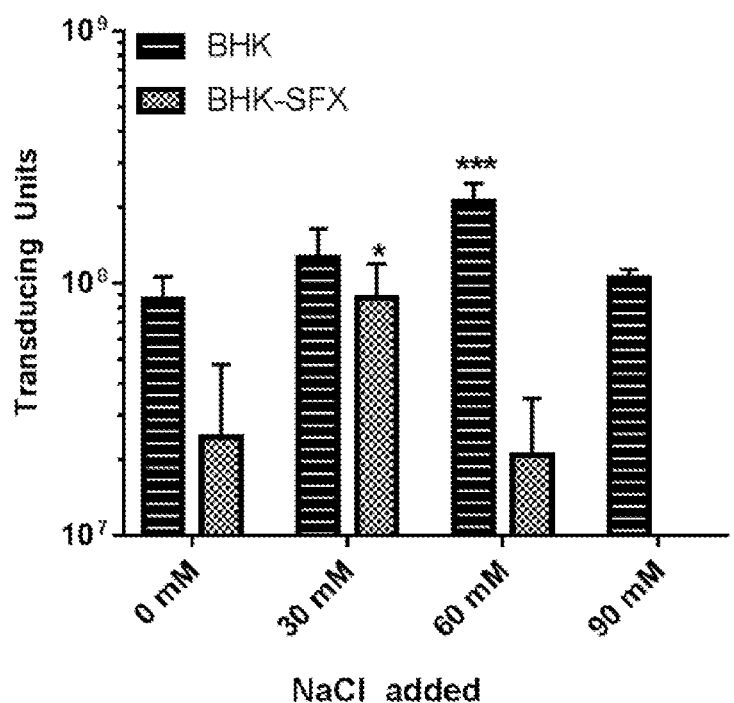
Figure 6D:
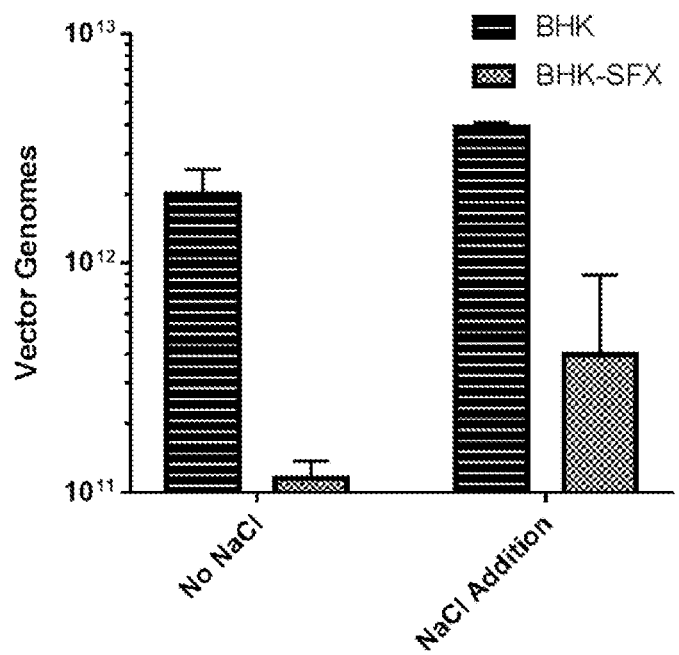

FIGS. 6A to 6D show increased rAAV9 production following sodium chloride supplementation for other rAAV serotypes, genes of interest, and/or cell types. Total transducing units (FIG. 6A) and total vector genomes (FIG. 6B) were evaluated for rAAV2-GFP, rAAV5-GFP, and rAAV9-Des-GAA produced by rHSV co-infection in shaker flasks (50 ml working volume) in the presence of increased sodium chloride concentration (n=2 for all). FIG. 6C shows the impact of increased sodium chloride on rAAV9-GFP production in BHK cells grown in DMEM with 5% FBS (BHK) or adapted to serum-free media (BHK-SFX). FIG. 6D shows the total rAAV9-GFP vector genomes produced in BHK and BHK-SFX cells by rHSV co-infection in the absence or presence of optimal salt supplementation (30 and 60 mM, respectively). (*p<0.05, ***p<0.001).

Figure 7A:
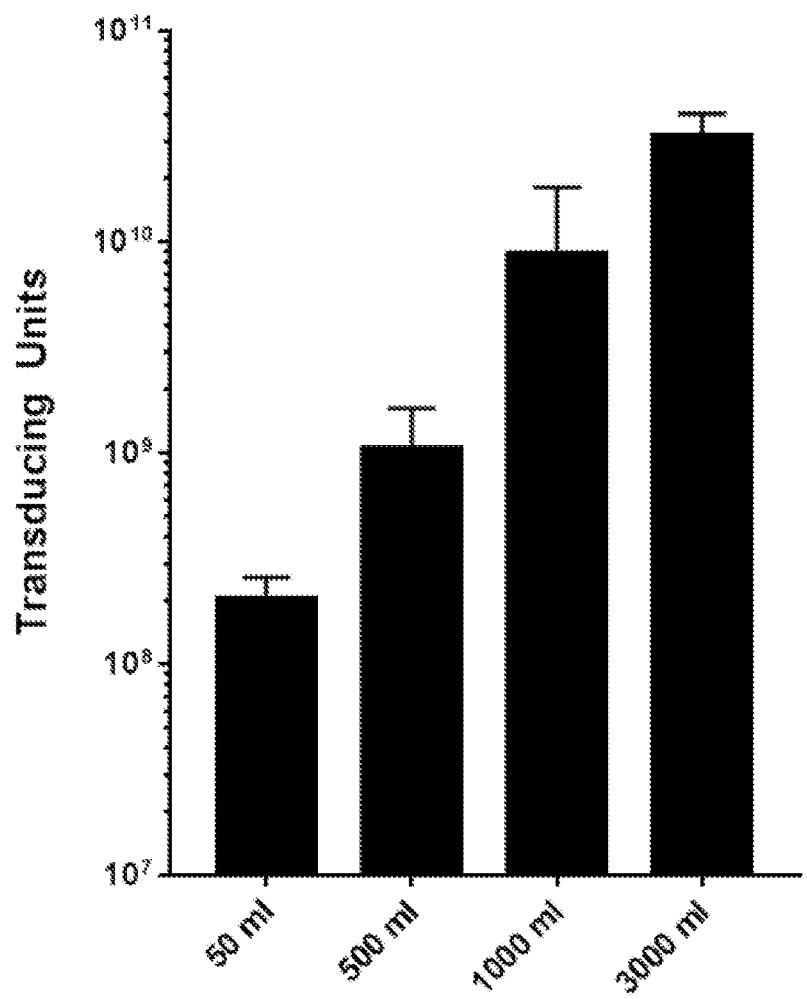
Figure 7B:
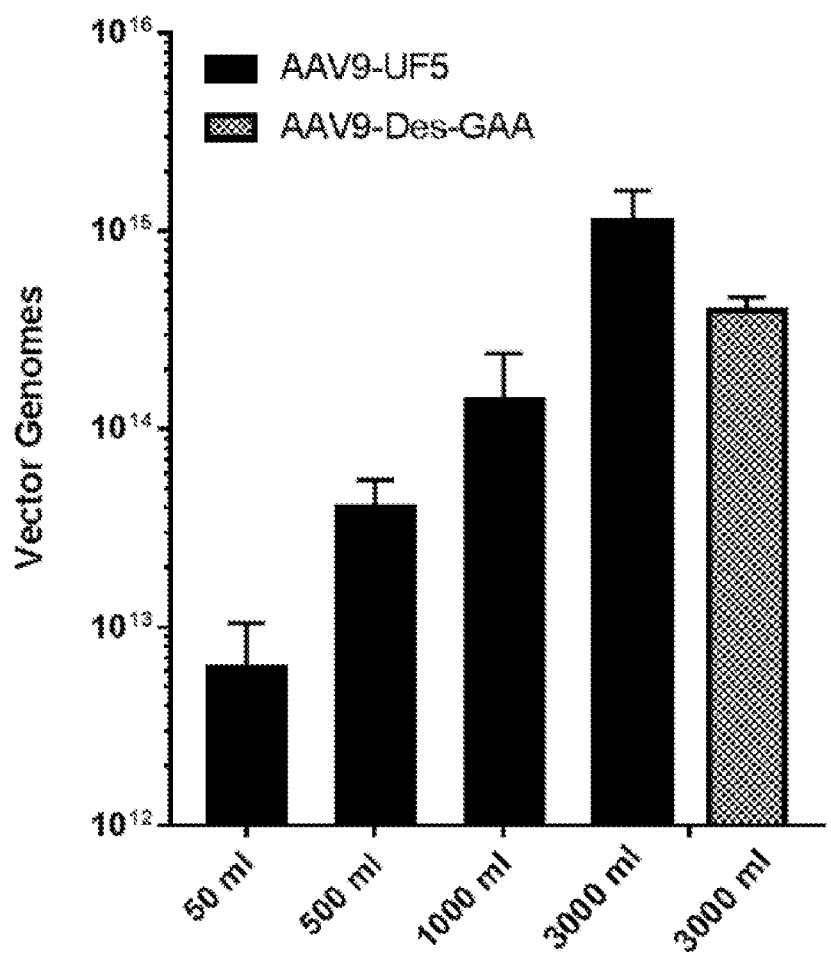

FIGS. 7A to 7C show scalability of rAAV production in EXPI293F™ cells. Transducing units for rAAV9-GFP (FIG. 7A) and total vector genomes for rAAV9-GFP and rAAV9-Des-GAA (FIG. 7B) were assessed in crude lysates from EXPI293F™ cultures ranging from 50 to 3000 mL. FIG. 8C shows total vector genome values represented as vectors genomes per cell at each scale.

Figure 8A:
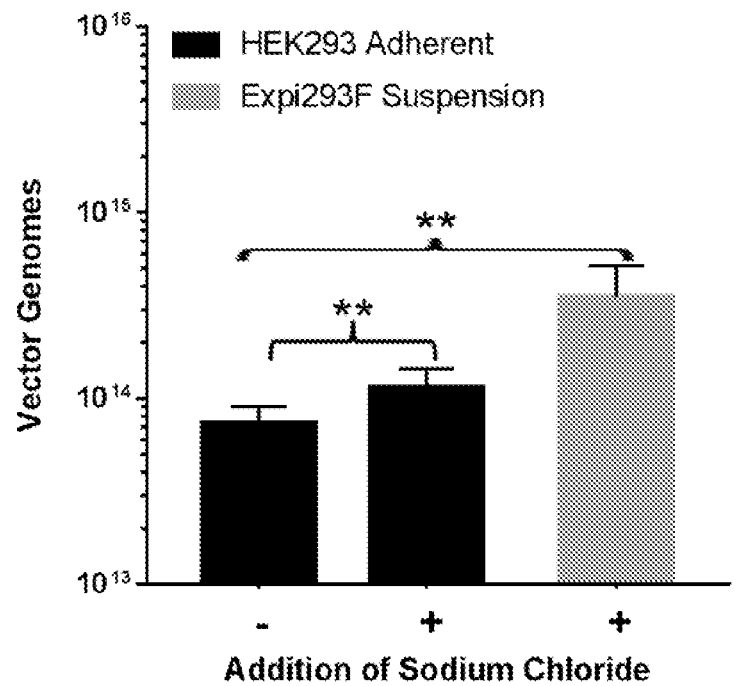
Figure 8B:
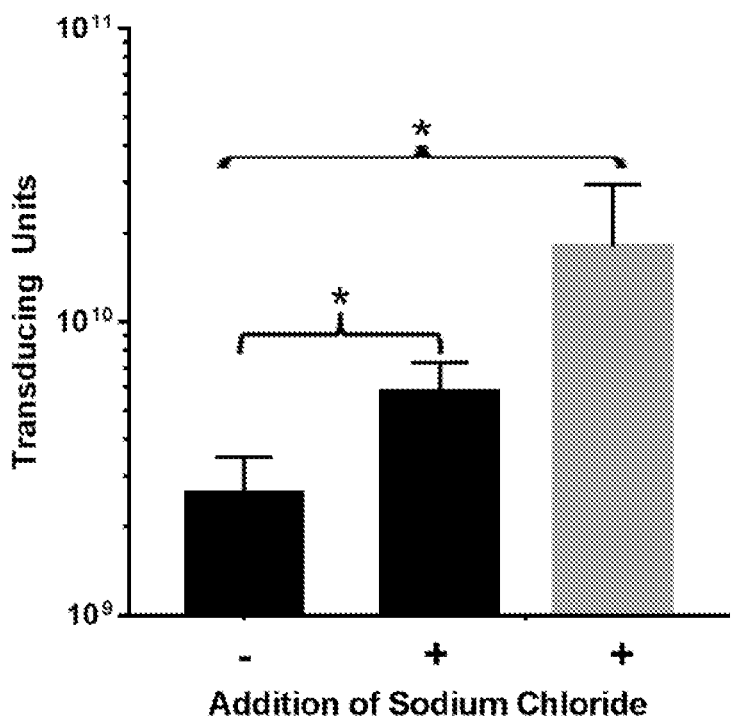
Figure 8C:
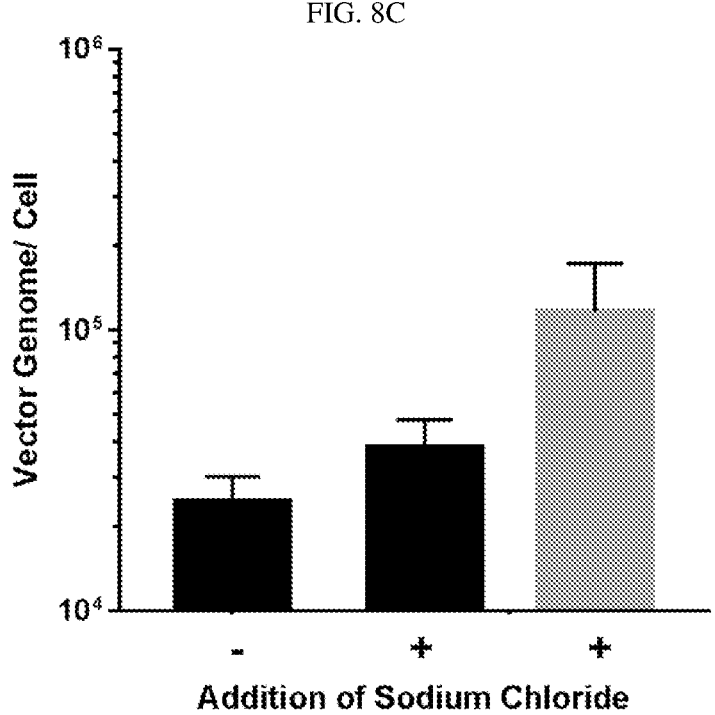
Figure 8D:
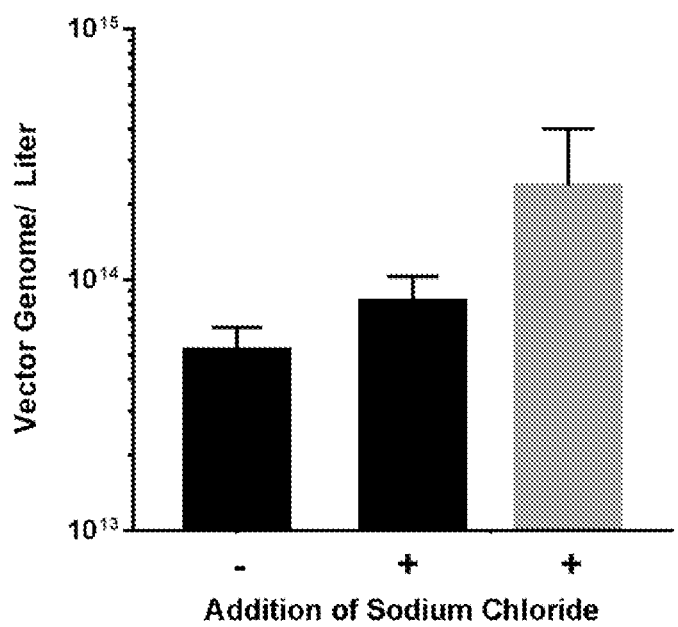
Figure 8E:
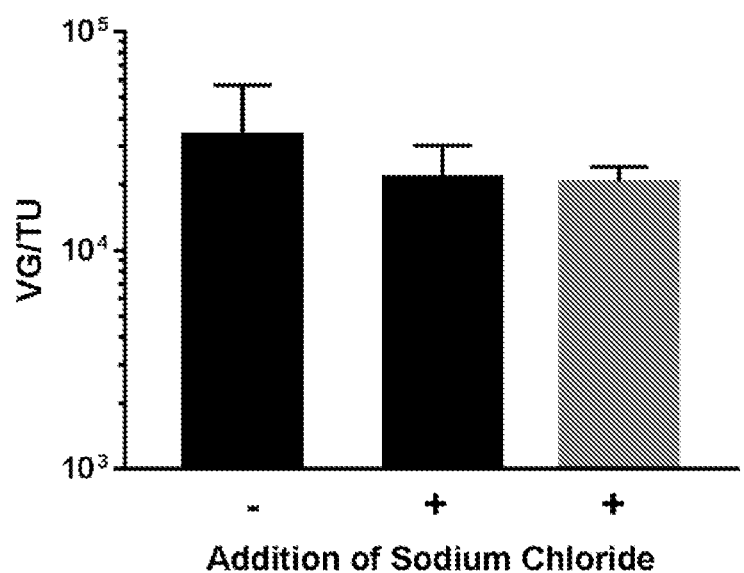
Figure 8F:
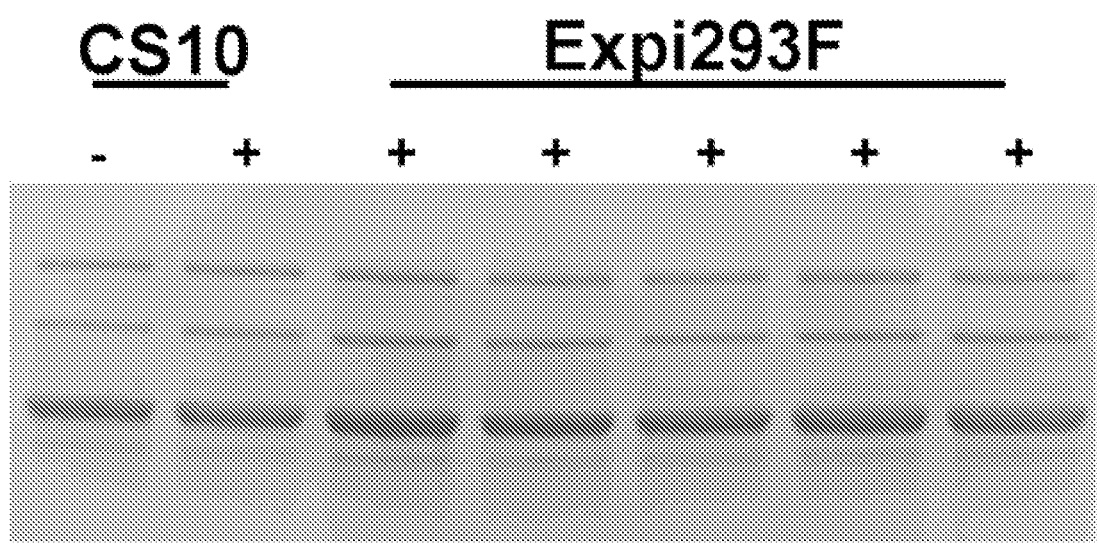

FIGS. 8A to 8F show characterization of rAAV vector made in EXPI293F™ suspension system. FIG. 8A and FIG. 8B show rAAV9-GFP was produced by rHSV infection in adherent HEK293 CS10® grown under optimal conditions (approximately 3×10$^9$ cells) either in DMEM containing 5% FBS alone (n=4) or supplemented with 60 mM sodium chloride (n=6), or in a 3 L suspension culture containing 3×10$^9$ EXPI293F™ cells (n=5). Total vector genome (FIG. 8A) and transducing unit (FIG. 8B) yields are shown. Total purified vector genomes are represented relative to units produced per cell (FIG. 8C) and per liter of media (FIG. 8D). Total vector genomes per transducing units ratios are shown (FIG. 8E). FIG. 8F shows Coomassie staining of rAAV9-GFP final stocks produced in HEK293 CS10® in the absence of salt supplementation (Lane 1), or supplemented with sodium chloride (Lane 2), or produced in EXPI 293F™ 3 L cultures supplemented with sodium chloride (Lanes 3-7). A total of 10$^{11}$ vg loaded per well. (*p<0.05, **p<0.01).

Figure 9:
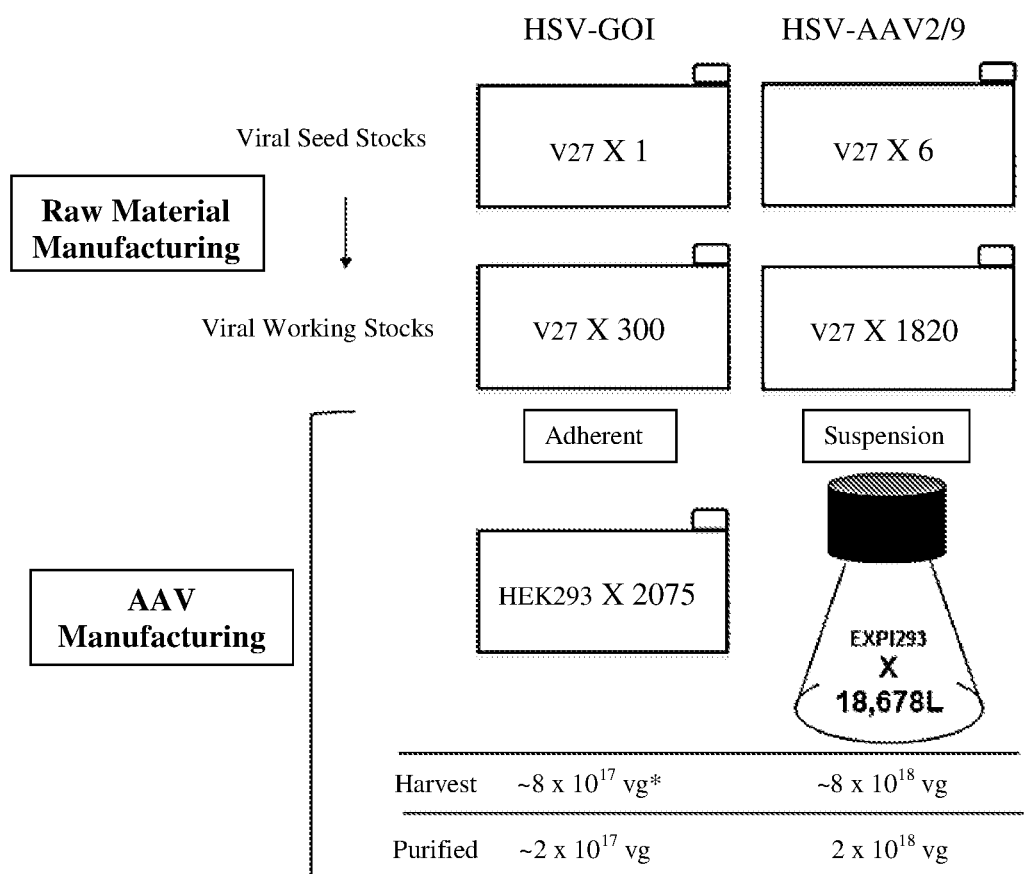

FIG. 9 shows theoretical HSV system scalability. Extrapolation was based on current average rHSV yields for the constructs. HSV stocks were produced from adherent V27 cells grown in 10 layer flasks (CS10®). Number of production units (CS10® for adherent or liter for suspension), as well as cell type (V27, HEK293 or EXPI293F™) are indicated for each step and were rounded for clarity. HSV-GOI and HSV-Rep2Cap9 Seed stocks were produced from 1 and 6 CS10®, respectively to support MOIs used in the adherent platform (2:12, respectively).

Figure 10:
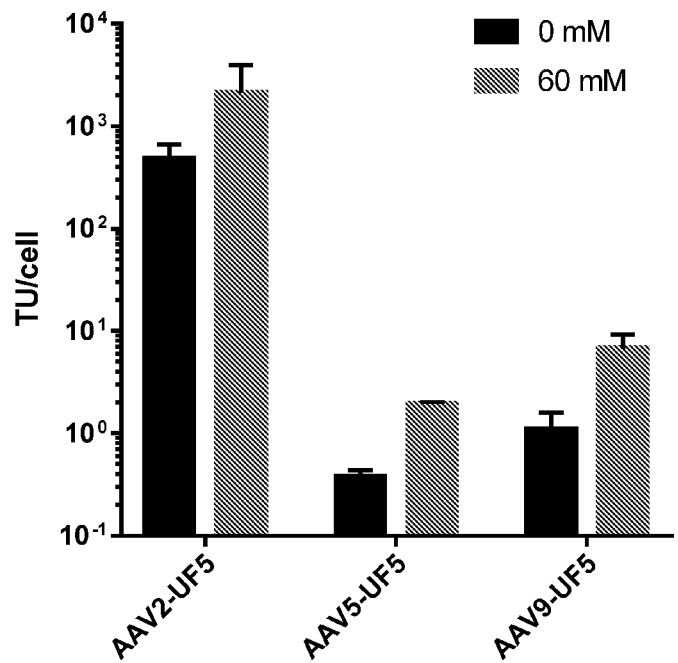

FIG. 10 shows increased rAAV9 production following sodium chloride supplementation for different rAAV serotypes and genes of interest. Transducing units per cell were evaluated for rAAV2-GFP, rAAV5-GFP, and rAAV9-GFP produced by rHSV co-infection in shaker flasks (5E7 cells at 1E6 c/mL in 50 ml working volume, MOI 2:4, 48 hours incubation) in the presence of increased sodium chloride concentration (60 mM supplementation) (n=2 for all).

Figure 11:
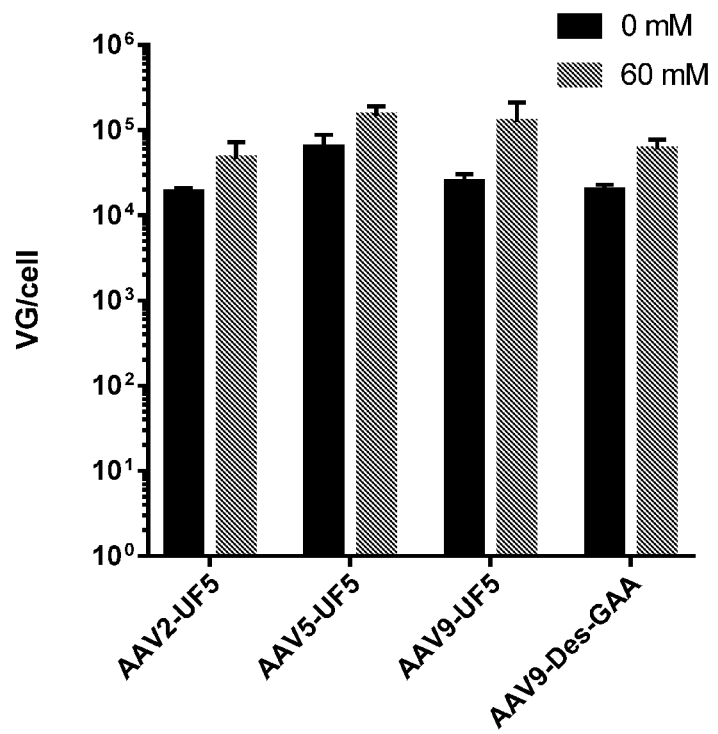

FIG. 11 shows increased rAAV9 production following sodium chloride supplementation for other rAAV serotypes and genes of interest. Vector genomes per cell were evaluated for rAAV2-GFP, rAAV5-GFP, rAAV9-GFP and rAAV9-Des-GAA produced by rHSV co-infection in shaker flasks (5E7 cells at 1E6 c/mL in 50 ml working volume, MOI 2:4, 48 hours incubation) in the presence of increased sodium chloride concentration (60 mM supplementation) (n=2 for all)

Figure 12:
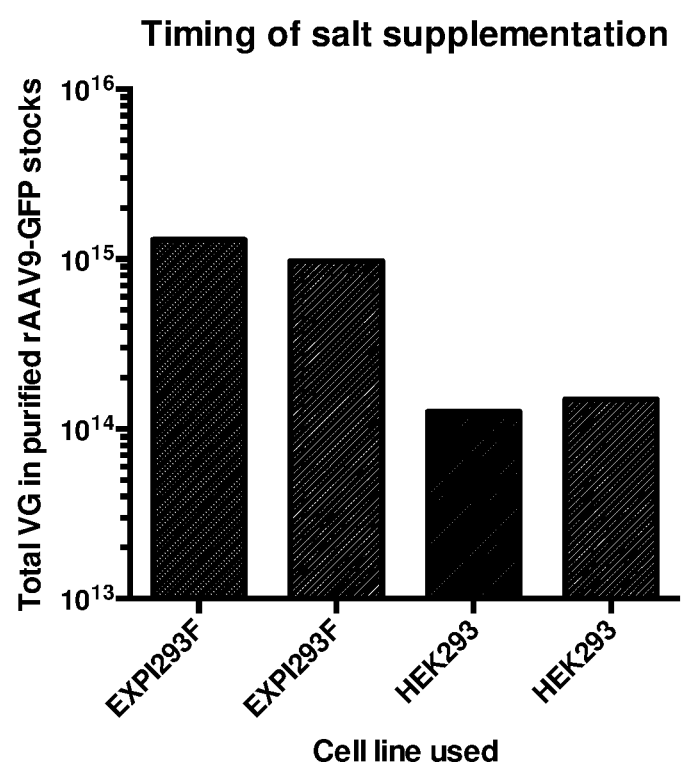

FIG. 12 shows that salt supplementation can occur 6 hours (gray lines bars) after HSV co-infection occurred both in adherent format (HEK293) or suspension format (EXPI293F™) without affecting the overall yield (Black bars, salt added at the time of HSV coinfection) as measured by the total vector genomes. HEK293 were infected at MOI 2:12 and EXPI293F™ cells were infected at MOI 2:4 and harvested after 48 hours. AAV9 particles were purified and stocks tittered for vector genomes.

Figures 13, 14:
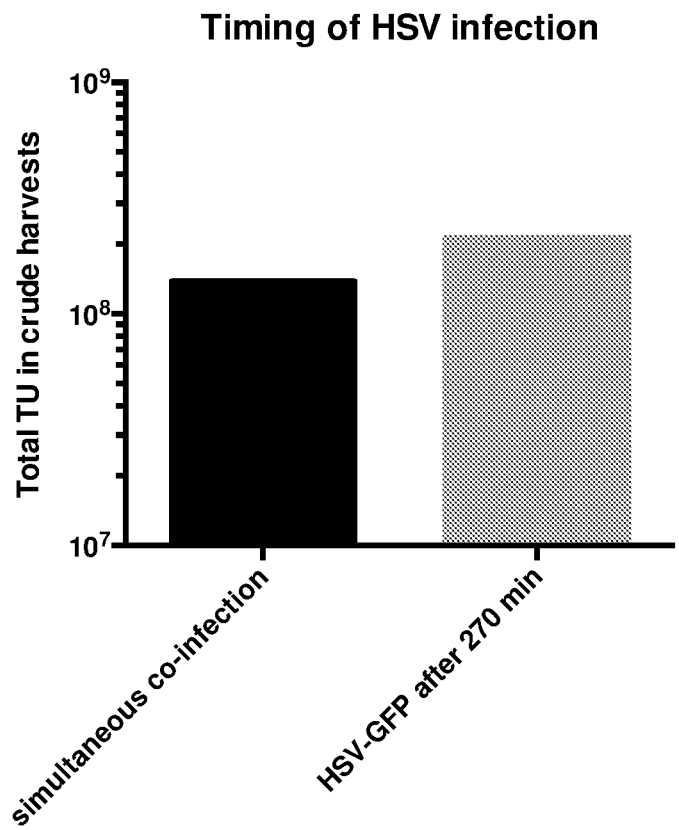

FIG. 13 shows effects of timing of HSV co-infection. HSV-GFP can be added up to 4½ hour (270 min) after HSV-AAV9 has been added to the production medium without negatively impacting the overall AAV yield, as measured by total transducing units in EXPI293F™ crude harvests. FIG. 14 shows that simultaneous coinfection is not required for optimal AAV production.

FIG. 14 shows the quality of rAAV9-GFP stocks is improved when produced in the HSV system in combination with salt supplementation and suspension-adapted EXPI293F™ cells: the percentage of full capsid (containing AAV9-GFP genome) and empty capsids as measured by AAV9 capsid proteins (ELISA) and vector genome titer (Q-PCR) are shown. AAV9 stocks produced in EXPI293F™ in the presence of 60 mM NaCl supplementation contains more full capsids than stocks prepared by transfecting or HSV in absence of salt.

Figure 15:
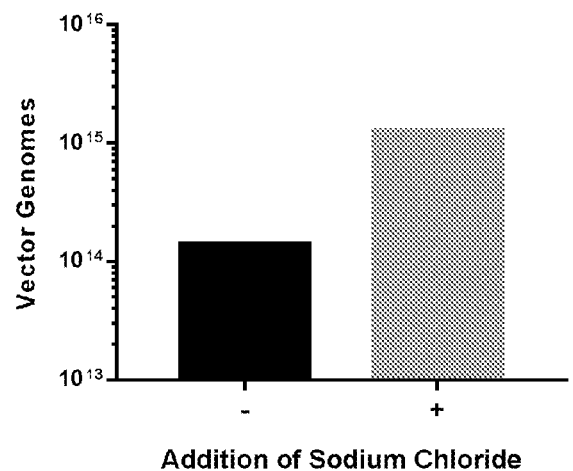

FIG. 15 shows the improved yields as a result of salt supplementation are also seen at large scale rAAV production levels. 3 L cultures were infected with rHSV-GFP at an MOI of 2:4 either in the absence (−) or presence (+) of sodium chloride to a final concentration of 60 mM, and total vector genomes were measured in the crude lysates. Production in a 3 L culture without the addition of sodium chloride resulted in 1.40×10$^{14}$ vg total production in crude lysates, or 4.63××10$^{13}$ vg/L. Comparatively, the rAAV yield was 9.1-fold higher in sodium chloride supplemented flasks infected in parallel.

Figure 16A:
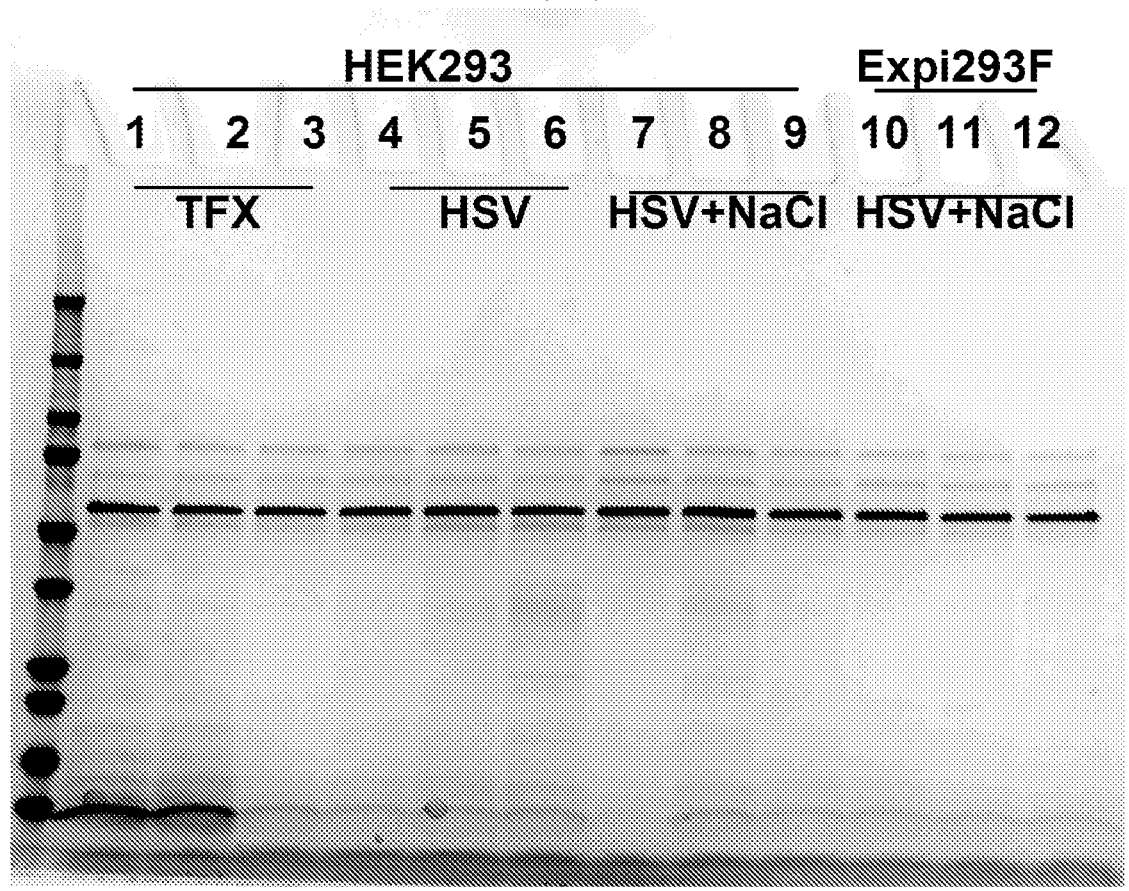
Figure 16B:
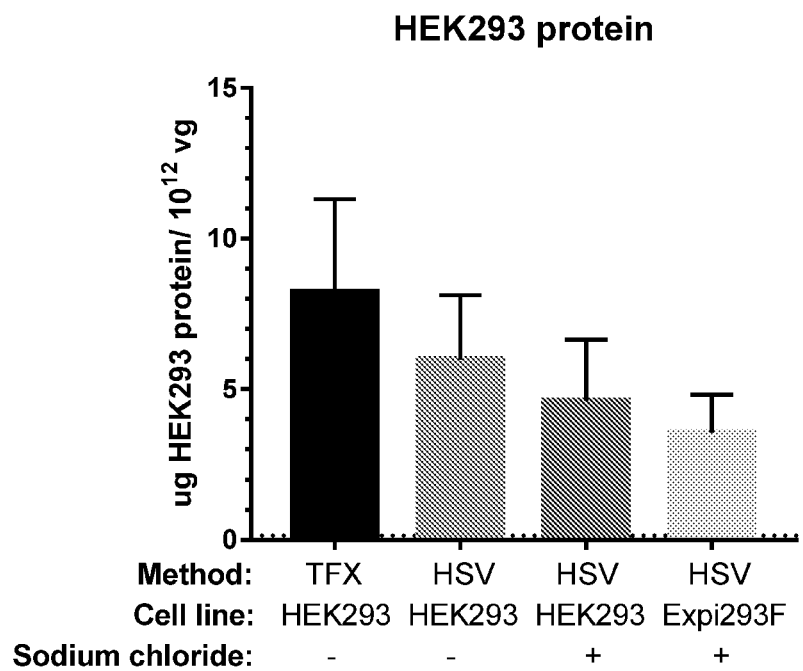
Figure 16C:
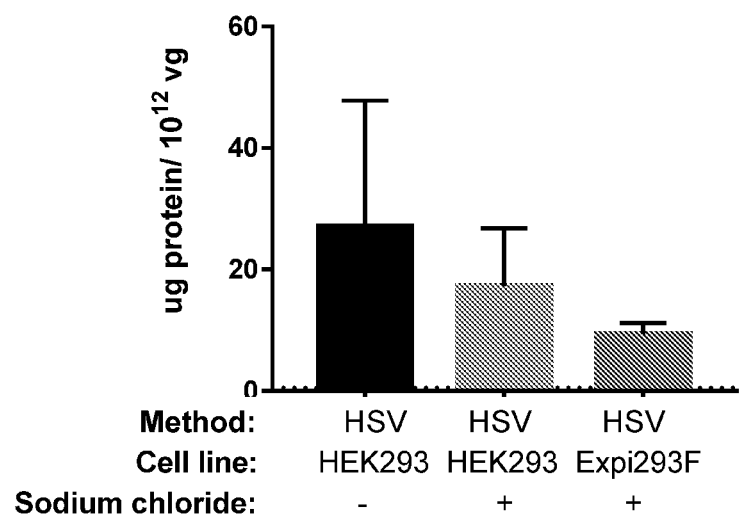

FIG. 16A to C shows that rAAV produced using EXPI293F™ cells in suspension cultures results in rAAV preparations that are of better quality and lower contamination. FIG. 16A shows total protein in rAAV prepared using transfection of adherent HEK293 cells, infection using HSV, infection using HSV and salt supplementation of HEK293 cells, and infection using HSV and salt supplementation in EXPI293F™ cells in suspension cultures. Vector preparations were diluted to 5×10$^{12}$ capsids per ml, and 32 µl of each sample was loaded per lane. Three samples from each group representing material made in HEK293 (lanes 1-9), and EXPI293F™ suspension (lanes 10-12) were analyzed. These represent transfection produced rAAV9-GFP (TFX, lanes 1-3), HSV-produced using the standard 2:12 gene of interest to helper ratios (HSV, lanes 4-6), HSV-produced at 2:12 with additional sodium chloride (HSV+NaCl, lanes 7-9), and HSV-produced at 2:4 in EXPI293F™ cells (HSV+NaCl, lanes 10-12). The arrows point to the 4 major virus proteins seen on coomassie staining of rAAV9. Additional bands indicate the presence of vector degradation or process impurities, both of which are decreased in EXPI293F™ vector preparations produced in the increased presence of sodium chloride. FIG. 16B shows total HEK293 protein measured in rAAV9 samples made in adherent HEK293 cells by transfection (TFX), HSV-produced using the standard 2:12 gene of interest to helper ratios (HSV), HSV-produced at 2:12 with additional sodium chloride (HSV+NaCl), or HSV-produced at 2:4 in EXPI293F™ cells (HSV+NaCl). Values are represented as µg of total protein per 10$^{12}$ vector genomes. FIG. 16C shows total HSV protein measured in rAAV9 samples made in adherent HEK293 cells by transfection (TFX), HSV-produced using the standard 2:12 gene of interest to helper ratios (HSV), HSV-produced at 2:12 with additional sodium chloride (HSV+NaCl), or HSV-produced at 2:4 in EXPI293F™ cells (HSV+NaCl). Values are represented as µg of total protein per 10$^{12}$ vector genomes.

DETAILED DESCRIPTION

As the effectiveness of rAAV-based therapies becomes more evident by clinical outcomes in a number of indications, so does the demand for scalable, more productive and high-yield producing methods of rAAV particle production. Furthermore, the need for these rAAV production methods to be GLP/GMP-compatible is pertinent for end use as clinical compounds.

Usually, rAAV production involves (1) culturing cells, (2) introducing AAV genes and any genes desired to be packaged to the cells, and (3) allowing the cells to produce or package rAAV. The last step is followed by harvesting rAAV particles and subsequent purification steps. AAV genes and any genes desired to be packaged into rAAV particles may be introduced to cells by either transfection methods (e.g., using plasmid vectors and a transfection agent) or infection methods (e.g., using a viral vector). Cells are said to be "transfected" or "infected" at the time when transfection or infection reagents (e.g. vectors) are first introduced to the cells. The media used in the three stages of rAAV production may be the same or different in one or more of the stages of production. Herein, media used in these stages of rAAV production are referred to as 'culture media', 'infection or transfection media', and 'producer media.'

The inventors of this disclosure have found that rAAV production can be improved by increasing the concentration of salt in media after the initial growth or culture phase, either before, at the time or of after infection or transfection.

Accordingly, provided herein are methods of improving rAAV production that are scalable and GLP/GMP-compatible, and that emphasize the influence that salt concentration in the media has on the rAAV particle production rate and resultant yields during rAAV production.

This disclosure also provides a novel rAAV production approach that combines the use of suspension-adapted HEK293 cells and infection of the cells using viral vectors (e.g., rHSV vectors) to introduce AAV proteins and DNA.

Improving rAAV Production by Increasing Salt Concentration in Media

Provided herein are methods of improving rAAV production in cells by increasing salt concentration in the media in which the cells are infected or transfected to introduce AAV rep and cap genes and/or genes to be packaged into rAAV particles (e.g., transfection or infection media). In some embodiments of any one of the methods provided herein, salt concentration is increased in media in which cells produce rAAV particles (e.g., producer media).

In some embodiments, the concentration of salt in transfection or infection media, producer media is increased by supplementing the transfection or infection media, producer media with salt. In some embodiments, salt is supplemented to media by adding salt in solid or crystalline form directly to the media. In some embodiments, a solution of salt is added to media to supplement it.

In some embodiments, concentration of salt is increased (e.g., by supplementing) in transfection or infection media alone. In some embodiments, concentration of salt is increased (e.g., by supplementing) in producer media alone (e.g., after transfection or infection of the cells). In some embodiments, concentration of salt is increased in transfection or infection media, and also in producer media. In some embodiments, salt concentration is increased in transfection or infection media immediately before, at, or immediately after the time of transfection or infection. Producer media may then be added to the transfection or infection media. In some embodiments, salt concentration of producer media that is added to transfection or infection media is increased either prior to, or after, addition to transfection of infection media. In some embodiments, transfection or infection media is exchanged for producer media (e.g., by centrifuging the cells). If salt concentration in producer media that replaces transfection or infection media is increased, it may be increased either prior to, at, or after the time the transfection or infection media is replaced with producer media.

In some embodiments, concentration of salt is increased in transfection or infection media, and in producer media. In some embodiments, two or more of the culture media, transfection or infection media, and producer media are the same. For example, culture media may be the same as transfection or infection media. Vectors (e.g., plasmids or viral vectors) used for infection or transfection may be introduced to cells without exchanging culture media for transfection or infection media, or without adding transfection or infection media. In some embodiments, transfection or infection media is the same as producer media. For example, no exchange or addition of media occurs after cells are transfected or infected. In some embodiments, all three of culture media, transfection or infection media, and producer media is the same.

It is to be understood that by stating that more than one media are "same", it is meant that each of all the components of the media in question are the same and in equal proportions or quantities. A non-limiting list of media components include buffering agents (e.g., phosphates or acetates), nutrients (e.g., proteins, peptides or amino acids), carbohydrates, essential metals and minerals, indicators for pH change, antimicrobial agents and gelling agents (e.g., agar).

It should be appreciated that while salt is a component of media, the identity of the particular salt/s and/or the salt/s concentration/s may be proprietary information belonging to a manufacturer and may thus be unknown to a user.

In some embodiments, a commercially available buffer is adapted for cell growth and increasing the salt (e.g., by adding salt) during the transfection/infection or production stages can be beneficial. For example, the reported sodium chloride concentration in DMEM of a commercial source may be 6.4 g/L (109.5 mM) but an increase in rAAV vector production may be observed when 60 mM of sodium chloride is added. This would correspond to a final concentration of approximately 169.5 mM. The concentration of sodium chloride observed in normal saline is 154 mM, suggesting salt supplementation may be ideal when a final concentration is close to, or higher than, normal or physiological levels. Through the inventors' work, it is found that a benefit in rAAV yield can be attained by salt supplementation even for medias for which the salt concentration is unknown.

As used herein, "rAAV vectors" are used synonymously with "rAAV particles" or may also mean nucleic acid vectors that are used to produce rAAV particles.

Yield Improvement rAAV yields may improve by using any one of the methods described herein compared to rAAV production processes that are same with the exception of change in salt concentration. In some embodiments, the yield of rAAV production involving salt concentration changes may increase by 1.2 to 20 times (e.g., 1.2-18, 2-15, 3-12, 5-10 or 6-8 times) compared to rAAV production processes wherein salt concentration is not changed.

Timing

In some embodiments, salt concentration is increased before infection or transfection of cells with AAV rep and cap genes, other helper genes and/or one or more genes of interest. For example, if culture media is exchanged for transfection or infection media, salt may be increased in the transfection or infection media (e.g., by supplementing) either immediately before transfection or infection, at the time of transfection of infection, or immediately after transfection or infection. In some embodiments, salt concentration may be increased in transfection or infection media (e.g., by supplementing) a few hours (e.g., 1-8, 2-6 or 3-4 hours) or a few minutes (e.g., 1-60, 5-45 or 15 to 30 minutes)

before transfection or infection. In some embodiments, salt concentration may be increased in transfection or infection media (e.g., by supplementing) a few hours (e.g., 1-8, 2-6 or 3-4 hours) or a few minutes (e.g., 1-60, 5-45 or 15 to 30 minutes) after transfection or infection. In some embodiments, salt concentration is increased in culture media (e.g., by supplementing) a few hours (e.g., 1-8, 2-6 or 3-4 hours) or a few minutes (e.g., 1-60, 5-45 or 15 to 30 minutes) before transfection or infection. In some embodiments, salt concentration is increased (e.g., by supplementing) at the beginning of the rAAV production process, when the cells are start culturing or in the growth phase. In some embodiments, salt concentration is increased in producer media (e.g., by supplementing) a few hours (e.g., 1-8, 2-6 or 3-4 hours) or a few minutes (e.g., 1-60, 5-45 or 15 to 30 minutes) after transfection or infection.

Decreasing Salt Concentrations

In some embodiments of any one of the methods disclosed herein, it is desired to increase the concentration of salt around the cells for a finite period of time and not the entire duration of rAAV production. Accordingly, in some embodiments, the concentration of salt is decreased in producer media by either diluting the media with media of a lower salt concentration or exchanging the media with one of a lower salt concentration. Of course, producer media that is replaced may be processed to harvest rAAV particles in the media. In some embodiments, the concentration of salt in producer media is decreased 0.5-10 hours (e.g., 0.5-8, 1-9, 2-6 or 3-4 hours) after infection or transfection of cells or after salt concentration in the media has been increased (e.g., by supplementing).

Salt

In some embodiments, a salt the concentration of which is increased in any one of the methods disclosed herein, is an inorganic salt. In some embodiments, the salt is an alkali halide. Alkali halides are salts comprised of an alkali metal (e.g., lithium, sodium, potassium, rubidium, and caesium) and a halogen (e.g., fluorine, chlorine, bromine, and iodine). In some embodiments, an alkali halide is sodium chloride (NaCl). In some embodiments, an alkali halide is comprised of an alkali metal selected from Li, Na, K, Rb, and Cs, and a halogen selected from F, Cl, Br, and I. In some embodiments, a salt is an alkaline earth halide. In some embodiments, an alkaline earth halide is comprised of an alkaline earth metal selected from Be, Mg, Ba, and Ca, and a halogen selected from F, Cl, Br, and I. In some embodiments, a salt is a metal selenide, metal hydroxide, metal oxide, metal phosphate, metal silicate, metal borate, metal carbonate, metal nitrate, or a metal sulfate.

In some embodiments, a salt the concentration of which is increased in any one of the methods disclosed herein, is one selected from the group consisting of aluminum chloride, magnesium chloride, lithium selenide, sodium carbonate, lithium chloride, sodium hydrogen phosphate, sodium metasilicate, strontium hydroxide, trisodium phosphate, potassium fluoride, magnesium sulfate, calcium chloride, sodium sulfate, aluminum sulfate, sodium tetraborate, magnesium sulfate, magnesium bromide, rubidium aluminum sulfate, barium hydroxide, potassium aluminum sulfate, magnesium nitrate, sodium hydrogen phosphate, nickel sulfate, zinc sulfate, beryllium sulfate, lithium nitrate, strontium chloride, zinc nitrate, sodium pyrophosphate, calcium bromide, copper sulfate, copper nitrate, aluminum nitrate, sodium tetraborate, silver fluoride, calcium iodide, lithium bromide, lithium iodide, strontium bromide, calcium nitrate, strontium iodide, sodium bromide and strontium nitrate.

In some embodiments, a salt the concentration of which is increased in any one of the methods disclosed herein, is an organic salt. Some non-limiting examples of suitable organic salts include sodium aluminum lactate, sodium acetate, sodium dehydroacetate, sodium butoxy ethoxy acetate, sodium caprylate, sodium citrate, sodium lactate, sodium dihydroxy glycinate, sodium gluconate, sodium glutamate, sodium hydroxymethane sulfonate, sodium oxalate, sodium phenate, sodium propionate, sodium saccharin, sodium salicylate, sodium sarcosinate, sodium toluene sulfonate, magnesium aspartate, calcium propionate, calcium saccharin, calcium d-saccharate, calcium thioglycolate, aluminum caprylate, aluminum citrate, aluminum diacetate, aluminum glycinate, aluminum lactate, aluminum methionate, aluminum phenosulfonate, potassium aspartate, potassium biphthalate, potassium bitartrate, potassium glycosulfate, potassium sorbate, potassium thioglycolate, potassium toluene sulfonate and magnesium lactate. In some embodiments, the concentration of more than one salt is increased in a culture media, transfection or infection media, or producer media.

In some embodiments of any one of the methods described herein, concentration of a supplemented salt in atransfection or infection media, or producer media is between 1-250 mM (e.g., 5-200 mM, 20-180 mM, 30-150 mM, 60-90 mM, 40-120 mM, 50-100 mM or 70-80 mM). The "concentration of a supplemented salt" is that which is added, and not the total concentration of a salt in a media.

In some embodiments, concentration of salt in transfection or infection media, or producer media is supplemented such that the total concentration of salt is between 125 and 250 mM (e.g., 130-200, 135-180, 140-185, 145-180).

In some embodiments, salt concentrations in culture media, transfection or infection media, and producer media is increased such that the concentration of salt in the transfection or infection media is higher than the concentration of salt in the culture media. In some embodiments, salt concentrations in culture media, transfection or infection media, and producer media is increased such that the concentration of salt in the transfection or infection media is higher than the concentration of salt in the culture media and the producer media. In some embodiments, concentrations of salt in transfection or infection media, and producer media is increased such that the concentrations of salt in the transfection or infection media, and in the producer media is higher than the concentration of salt in the culture media.

Cells and Culture Formats

It should be appreciated that any cell or cell line that is known in the art to produce rAAV particles can be used in any one of the methods disclosed herein. In some embodiments, a cell used to produce rAAV in any one of the methods disclosed herein is a mammalian cell. Non-limiting examples of mammalian cells that can be used to produce or package rAAV are HEK293 cells, COS cells, HeLa cells, HeLaS3, BHK cells, CHO cells or PER.C6® (see, e.g., ATCC® CRL-1573™, ATCC® CRL-1651™, ATCC® CRL-1650™, ATCC® CCL-2, ATCC® CCL-2.2, ATCC® CCL-10™, or ATCC® CCL-61™). In some embodiments, a cell used to produce rAAV particles is an insect cell. An example of insect cells includes Sf9 cells (see, e.g., ATCC® CRL-1711™).

In some embodiments, cells are adapted to be cultured in suspension culture. Methods of adapting adherent cells for suspension culture are known in the art.

As described herein, inventors of this disclosure have discovered that salt (e.g., NaCl) is a critical component of an inoculum that improves yields in the production of rAAV in suspension-adapted cells, but that is not adjusted routinely. However, it should be appreciated that methods provided herein can be advantageous in the production of rAAV in adherent cells as well. Accordingly, cells in any one of the methods described herein may be cultured in adherent format (e.g., in cell culture dishes or T-flasks, or a multilayer tissue culture flask such as a Corning CellSTACK®, Corning HYPERStack® or Nunc™ EasyFill™ Cell Factory™) or in suspension culture (e.g., in a bioreactor such as a Wave bioreactor, a shaker flask, a spinner flask or a cellbag). In some embodiments, cells are attached to a substrate (e.g., microcarriers) that are themselves in suspension in a media.

Transfection or Infection of Cells to Introduce AAV Rep and Cap Proteins and/or One or More Genes of Interest There are numerous methods by which AAV rep and cap genes, other AAV helper genes, and one or more genes of interest can be introduced into cells to produce or package rAAV. In some embodiments of any one of the rAAV production methods disclosed herein, AAV rep and cap genes and one or more genes of interest can be introduced into cells by transfection of one or more plasmid vectors harboring AAV rep and cap genes and one or more genes of interest. In some embodiments of any one of the rAAV production methods disclosed herein, AAV rep and cap genes and one or more genes of interest can be introduced into cells by infection of viral vectors harboring AAV rep and cap genes and one or more genes of interest can be introduced into cells.

AAV rep and cap genes may be harbored by one or even more than one (e.g., two or three) vectors (e.g., plasmids or viral vectors). Similarly, more than one (e.g., two or three) genes of interest (e.g., a gene encoding a therapeutic protein) may be harbored by one or even more than one (e.g., two or three) vectors (e.g., plasmids or viral vectors).

Plasmids carrying AAV rep and cap genes, or other genes needed for rAAV packaging such as E1a gene, a E1b gene, a E4 gene, a E2a gene, and a VA gene are also referred to as helper plasmids. Some non-limiting examples of helper plasmid vectors that are commercially available are pDF6, pRep, pDM, pDG, pDP1rs, pDP2rs, pDP3rs, pDP4rs, pDP5rs, pDP6rs, pDG(R484E/R585E), and pDP8.ape plasmids. In some embodiments, a viral vector is a retroviral vector, a lentiviral vector, or an adenoviral vector. In some embodiments, a viral vector is a recombinant herpes simplex virus vector (rHSV vector). Helper genes other than rep and cap genes may be harbored by the vectors harboring rep and cap genes or a gene of interest. In some embodiments, helper genes other than rep and cap genes are harbored on vectors other than the ones harboring rep and cap genes or a gene of interest.

Molecular biology techniques to develop plasmid or viral vectors (eg., rHSV or baculovirus vectors) with either AAV rep and cap genes or one or more genes of interest are commonly known in the art.

It is to be understood that any combination of vectors can be used to introduce AAV rep and cap genes and one or more genes of interest to a cell in which rAAv particles are to be produced or packaged. For example, a first rHSV encoding a gene of interest flanked by AAV inverted terminal repeats (ITRs), and a second rHSV encoding AAV rep and cap genes can be used. In some embodiments, a combination of transfection and infection is used by using both plasmid vectors as well as viral vectors (e.g., adenovirus). In some embodiments, one or more helper genes is constitutively expressed by the cells and does not need to be transfected on infected into the cells.

An AAV rep gene encodes rep proteins Rep78, Rep68, Rep52 and Rep40. An AAV cap gene encodes capsid proteins VP1, VP2 and VP3.

It should be appreciated that AAV rep, cap and other helper genes (e.g., E1a gene, E1b gene, E4 gene, E2a gene, or VA gene) can be of any AAV serotype. Similarly, AAV ITRs can also be of any AAV serotype. For example, in some embodiments, AAV ITRs of any one of the methods disclosed herein are AAV-2 ITRs. In some embodiments, AAV ITRs are from AAV-1, AAV-3, AAV-4, AAV-5, AAV-6, AAV-7, AAV-8, AAV-9, AAV-10, AAV-11, AAV-12 or other AAV serotypes (e.g., a hybrid serotype harboring sequences from more than one serotype). In some embodiments, AAV cap gene is an AAV-9, AAV-2 or AAV-5 cap gene. In some embodiments, an AAV cap gene is from AAV-1, AAV-3, AAV-4, AAV-5, AAV-6, AAV-7, AAV-8, AAV-9, AAV-10, AAV-11, AAV-12 or other AAV serotypes (e.g., a hybrid serotype harboring sequences from more than one serotype). In some embodiments, AAV rep and cap genes for the production of a rAAV particle is from different serotypes. For example, the rep gene can be from AAV 2 whereas the cap gene can be from AAV-9.

In some embodiments, the rep or cap or, rep and cap genes are operably linked to a promoter. A promoter may be constitutive, inducible or synthetic. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A and cytomegalovirus (CMV) promoters. Non-limiting examples of constitutive mammalian promoters include various housekeeping gene promoters, as exemplified by the β-actin promoter (e.g., chicken (3-actin promoter) and human elongation factor-1 α (EF-1α) promoter. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline. Synthetic promoters are also contemplated herein. A synthetic promoter may comprise, for example, regions of known promoters, regulatory elements, transcription factor binding sites, enhancer elements, repressor elements, and the like.

A Method for Improving the Quality of rAAV Preparations

The quality of an rAAV preparation can be assessed using various parameters, for example the yield of rAAV particles, concentration of rAAV particles, infectivity of the rAAV particles, the percentage of particles that carry the gene of interest (or lack of empty capsids), or contamination by bacterial or fungal elements, contamination by either proteins from the cells used to prepare rAAV (e.g., HEK293 cells), or a virus used to infect the cells used to prepare rAAV (e.g., HSV to introduce rep or cap protein to the cells). Another factor by which the quality of an rAAV preparation is assessed is the degradation of rAAV particles. Degradation or rAAV can be analyzed using various methods known in the art to determine the size of rAAV particle proteins. For example, proteins in a preparation of rAAV can be run on an SDS gel and interrogated for size. Chromatography or light scattering techniques may also be used to determine size of proteins and particles.

In some embodiments, quality of an rAAV preparation is improved by infecting the cells used for rAAV production rather than transfecting them with necessary AAV genes (e.g., rep, cap and helper genes). In some embodiments, quality of an rAAV preparation is improved by supplementing with salt the media in which cells produce rAAV. In some embodiments, quality of an rAAV preparation is improved by supplementing with salt the media in which cells are transfected or infected, whether the cells are cultured in adherent form or in suspension.

A Method for Producing rAAV Using Suspension-Adapted Cells with HSV Infection

In some aspects, provided herein is a method for producing rAAV comprising the use of suspension-adapted cells (e.g., suspension-adapted HEK293 cells). In some embodiments, the method comprises infecting suspension-adapted cells (e.g., suspension-adapted HEK293 cells) with one or more viral vectors (e.g., rHSV) to introduce AAV rep, cap and helper genes and optionally one or more genes of interest. In some embodiments, a method comprises co-infecting suspension-adapted cells (e.g., suspension-adapted HEK293 cells) with a first rHSV encoding a gene of interest flanked by AAV ITRs, and a second rHSV encoding AAV rep and cap genes.

In some embodiments, any one of the methods involving suspension-adapted cells (e.g., suspension-adapted HEK293 cells) as provided herein further comprises isolating rAAV particles from infected cells and/or the media in which the cells produced rAAV particles.

In some embodiments, suspension-adapted HEK293 cells are derived from adherent HEK293 cells. In some embodiments, suspension-adapted cells (e.g., suspension-adapted HEK293 cells) are obtained from a commercial source (e.g., EXPI293F™ cells). In some embodiments, suspension-adapted cells (e.g., suspension-adapted HEK293 cells) are cultured, infected or incubated to produce rAAV particles in a shaker flask, a spinner flask, a cellbag, or a bioreactor (e.g., a Wave reactor). In some embodiments, one or more of the AAV rep or cap genes are introduced or delivered to suspension-adapted cells using more than one second rHSV. For example, two rHSVs, one that harbors a rep gene and the other than harbors a cap gene can be used. Other helper genes (e.g., E1a gene, E1b gene, E4 gene, E2a gene, or VA gene) can be harbored on the same rHSV that harbors the rep and/or cap genes or on a separate rHSV vector.

It should be appreciated that AAV rep, cap and other helper genes (e.g., E1a gene, E1b gene, E4 gene, E2a gene, or VA gene) can be of any AAV serotype. Similarly, AAV ITRs can also be of any AAV serotype. For example, in some embodiments, AAV ITRs of any one of the methods disclosed herein are AAV-2 ITRs. In some embodiments, AAV ITRs are from AAV-1, AAV-3, AAV-4, AAV-5, AAV-6, AAV-7, AAV-8, AAV-9, AAV-10, AAV-11, AAV-12 or other AAV serotypes (e.g., a hybrid serotype harboring sequences from more than one serotype). In some embodiments, AAV cap gene is an AAV-9, AAV-2 or AAV-5 cap gene. In some embodiments, an AAV cap gene is from AAV-1, AAV-3, AAV-4, AAV-5, AAV-6, AAV-7, AAV-8, AAV-9, AAV-10, AAV-11, AAV-12 or other AAV serotype (e.g., a hybrid serotype harboring sequences from more than one serotype).

In some embodiments, rep and cap genes for the production of a rAAV particle is from different serotypes. For example, the rep gene can be from AAV 2 whereas the cap gene can be from AAV-9.

In some embodiments, the rep or cap or, rep and cap genes are operably linked to a promoter. In some embodiments, a gene of interest is operably linked to a promoter. In some embodiments, a rep gene, cap gene, and/or gene of interest may be operably linker to their natural promoter, or alternatively a different promoter. In some embodiments, a promoter may be constitutive, inducible or synthetic as described above.

In some embodiments, a gene of interest encodes a therapeutic protein. In some embodiments, a therapeutic gene encodes an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic proteins, a nuclease or other protein used for gene editing, an Fc-fusion protein, an anticoagulant, a nuclease, guide RNA or other nucleic acid or protein for gene editing.

In some embodiments, a therapeutic protein is therapeutic for lysosomal storage disease. In some embodiments, a therapeutic protein is therapeutic for a neurological disability, a neuromotor deficit, a neuroskeletal impairment or a neuromuscular disease.

In some embodiments, a therapeutic protein is therapeutic for a muscular disability or dystrophy, a myopathy or a cardiomyopathy.

Other Parameters Influencing rAAV Production and Yield

It is to be understood that any one of the methods involving increasing salt concentration in media and using suspension-adapted HEK293 cells for rAAV production can be optimized for other parameters. Non-limiting examples of such parameters are multiplicity of infection during infection, cell density, shaker speed of suspension cultures and media pH at different stages.

EXAMPLES

Example 1. Production of AAV9-GFP in Suspension-Adapted HEK293 Cells

Cell lines described in Table 1 were co-infected with first and second rHSV as described herein. Reagents and Materials described in Tables 2 and 3, respectively were used. Approximately 1E8 cells were resuspended in fresh medium at 1E6 c/mL on the day of infection. Different cell lines and medium combinations were used. After coinfection with the rHSV stocks, the cells were harvested by centrifugation and virus released by a series of 3 freeze/thaws in lysis buffer (Tris, NaCl, pH 8.5). Lysates were benzonased treated for 30 minutes at 37 C and clarified by centrifugation. Infectious titers were assayed by green cell assay (also known as transduction assay): C12 cells were infected by serial dilution of the AAV9-containing crude lysates and wtAd5. GFP-expressing cells were counted after 48 hours and transducing titers calculated based on the dilution used.

Four different cell conditions were compared (s293-VC-suspension adapted: suspension adapted HEK293 cells grown in Joklik medium containing 5% FBS and 1% AA; s293-VC EXPI™: suspension adapted HEK293 grown in serum-free medium; EXPI293F™ cells grown in serum-free EXPI293™ medium; and BHK21 cells grown in DMEM 5% serum, 1% AA).

Figure 2:
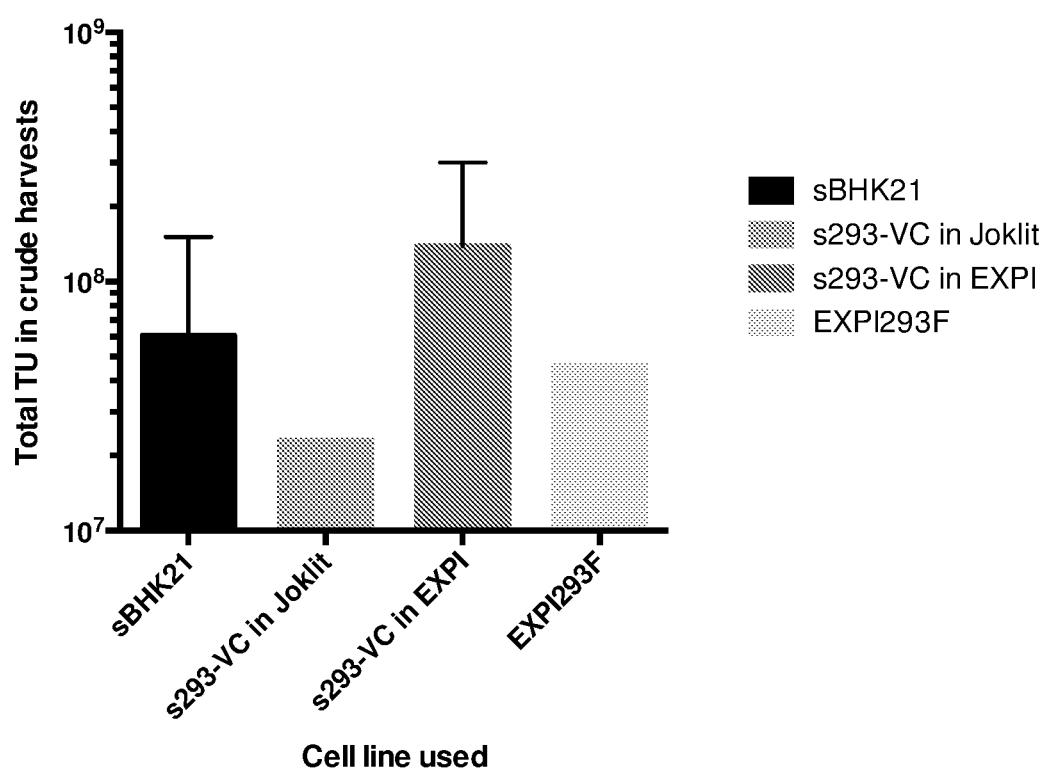
FIG. 2 shows production of rAAV particles comprising GFP in different cells types. Suspension adapted EXPI293F™ cells and suspension adapted BHK21 cells obtained from commercial vendors; suspension adapted s293-VC were generated in the laboratory from adherent HEK293. EXPI293F™ were grown in serum-free EXPI293™ medium; BHK21 were grown in DMEM, 5% serum, 1% Antibiotic/Antimycotic; s293-VC were grown in Joklik medium containing 5% FBS and 1% AA or in serum-free EXPI293™ medium.

Production of rAAV (AAV9-GFP, expressing GFP) was evaluated and the results are shown in Table 4 and FIG. 2.

TABLE 1

Cell lines

| Cell lines | Vendor | Catalog number |
|---|---|---|
| s293-VC - suspension adapted | N/A | N/A |
| S293-VC Expi -serum free adapted | N/A | N/A |
| EXPI293F ™ | Life Technologies | A14527 |
| BHK21 C13-2P | Sigma | 84111301-1VL |

TABLE 2

Reagents

| SMEM Joklik's modification | Lonza | 04-719Q (1 L) |
|---|---|---|
| EXPI293 Expression medium | Gibco - Life Technologies | A14351-01 (1 L) |
| SFM4Transfx-293 | Hyclone | SH30860.02 |
| Fetal Bovine Serum | Corning | |
| Dulbecco's Modifications of Eagle's Medium | Corning - Cellgro | 10-017-CM (1 L) |
| Antibiotic/Antimycotic | Gibco - Life Technologies | 15240-062 (100 mL) |

TABLE 3

Materials

| Reagent | Vendor | Catalog number |
|---|---|---|
| 125 mL Spinner Flask | Corning | 3152 |
| 500 mL Spinner Flask | Corning | 3153 |
| 125 ml Shaker Flask | Corning | 431143 |
| 500 ml Shaker Flask | Corning | 431145 |
| 2000 ml Shaker Flask | Corning | 431255 |
| 5000 ml Shaker Flask | Corning | 431685 |
| Magnetic stirrer | Wheaton | Model # W900701---A |
| Incubator | Infors-HT | I10002P |
| Incubator | Forma | Model # |

TABLE 4

Results

| Cell lines | Average | SDEV | % CV | Number of experiments |
|---|---|---|---|---|
| BHK21 | 6.08E7 | 9.03E7 | 149 | 16 |
| s293-VC | 2.3E7 | N/A | N/A | 1 |
| s293-VC/Expi | 1.39E8 | 1.61E8 | 116 | 5 |
| EXPI293F ™ | 4.6E7 | N/A | N/A | 1 |

REFERENCES

Knipe, D. "The Role of Viral and Cellular Nuclear Proteins in Herpes Simplex Virus Replication," Advances in Virus Research, vol. 37: 85-123, 1989.

Conway, et al., "High-Titer Recombinant Adeno-Associated Virus Production Utilizing a Recombinant Herpes Simplex Virus Type I Vector Expressing AAV-2 Rep and Cap," Gene Therapy, vol. 6: 986-993, 1999.

Buller, et al., "Herpes Simplex Virus Types 1 and 2 Completely Help Adenovirus-Associated Virus Replication," Journal of Virology, vol. 40: 241-247, 1981.

McCarthy, et al., "Herpes Simplex Virus Type 1 ICP27 Deletion Mutants Exhibit Altered Patterns of Transcription and are DNA Deficient," Journal of Virology, vol. 63, 18-27, 1989.

Sandri-Goldin, et al., "A Herpesvirus Regulatory Protein Appears to Act Post-Transcriptionally by Affecting mRNA Processing," Genes & Development, vol. 6: 848-863, 1992.

Rice, et al., "Genetic Evidence for Two Distinct Transactivation Functions of the Herpes Simplex Virus a Protein ICP27," Journal of Virology, vol. 64, 1704-1715, 1990.

Weindler, et al., "A Subset of Herpes Simplex Virus Replication Genes Provides Helper Functions for Productive Adeno-Associated Virus Replication," Journal of Virology, vol. 65, 2476-2483, 1991.

Example 2. Sodium Chloride Enhances rAAV Production in a Serum-Free Suspension Manufacturing Platform Using the Herpes Simplex Virus System Reported here is a scalable production method that utilizes suspension-adapted HEK293 cells combined with a serum and animal-component free media that enables production of high titer, high potency and high quality rAAV vector preparation in a GLP/GMP-compatible overall process.

Materials and Methods

Cell Lines.

Suspension BHK21C13-2P (BHK) were obtained from Sigma-Aldrich (St. Louis, Mo.) and maintained in Dulbecco's Modification of Eagles Medium (Hyclone, GE Healthcare, Logan, Utah) supplemented with 5% FBS (Corning, Corning, N.Y.) and 1% antibiotic/antimycotic (Gibco, ThermoFisher Scientific, Waltham, Mass.). BHK-SFX were created by gradual media exchange into serum-free SFM4Transfx-293 over 6 passages (Hyclone, GE Healthcare, Logan, Utah). BHK-SFX cells were grown 3 passages in 100% serum-free media prior to rAAV production. EXPI293F™ were purchased from ThermoScientific and maintained in EXPI293F™ media (ThermoScientific, Waltham, Mass.). V27 (a gift from Dr. Knipe, Harvard, Mass.) and C12 (a gift from Dr. P. Johnson, Children's Hospital of Philadelphia, Pa.) cells were maintained in DMEM supplemented with 5% FBS, and 50 µg/ml Geneticin (Sigma, St. Louis, Mo.).

rHSV Construction and Production.

Recombinant herpes viruses were generated by homologous recombination as previously reported[12, 16, 17]. Recombinant rHSV-Des-GAA was constructed from plasmid pTR-Des-hGAA reported containing the human acid alpha-glucosidase (GAA) gene under the promoter/enhancer sequence of the human DESMIN gene[18]. rHSV stocks were prepared on V27 at ~80-90% confluency (~7-9×10$^8$ cells per CS10® (Corning)). rHSV was added to the medium at an MOI of 0.15 pfu/cell. At 72-96 hours post-infection, cells were lysed in 0.6M NaCl (Lonza, Allendale, N.J.), harvested, and cell debris removed by centrifugation. rHSV-containing lysate was concentrated approximately 10-fold by Tangential Flow Filtration using TangenX™ SIUS™-300 kDda (Cat #XP300L01L, TangenX™, Shrewsbury, Mass.). rHSV stocks were supplemented with glycerol to a 5% final concentration (ThermoFisher), aliquoted, and stored frozen at negative −80° C.

HSV-Specific Plaque Assay rHSV infectious titers were assessed by a traditional plaque assay. V27 cells were seeded at $1.2 \times 10^5$ cells per well in 24-well plates (Corning). Serial dilutions of the rHSV stocks were added to the cells and incubated for 1.5-2 hours. The inoculate was removed and DMEM containing 0.8% Agar (LMT Invitrogen, ThermoFisher Scientific, Waltham, Mass.) was poured in each well. Plaques were counted by microscopic examination at 72 hours post-infection.

rAAV Production and Purification

AAV production. EXPI293F™ or BHK cells were co-infected at the indicated multiplicity of infection (MOI) with rHSV stocks containing a gene of interest (GFP or GAA) and a second rHSV containing AAV Rep2Cap2, Rep2Cap5, or Rep2Cap9. Unless noted, cells were infected for 48 hours and collected by centrifugation. Cell pellets were lysed and analyzed as either crude preparations or purified as described below. For media supplementation experiments, cells were added to shaker flasks in 80% of the final media volume and supplemented with the additional 20% of media containing sodium chloride, FBS, or glycerol, or a combination of the three, at the reported concentrations. Adherent HEK293 rAAV production was performed as previously described[12].

AAV9 purification. For small scale experiments, cells were pelleted by centrifugation and lysed in a 50 mM Tris and 150 mM sodium chloride lysis buffer at pH 8.5. Following 3 freeze-thaw cycles, lysates were treated with Benzonase® for 30 minutes at 37° C. and clarified by centrifugation. For large scale purification, AAV was purified from cell pellets as previously described[19]. Briefly cells were lysed and lysates were digested with Benzonase® (EMD Millipore, Billerica, Mass.) (crude lysate), clarified by protein flocculation and centrifugation, and then by anion-exchange chromatography using HiPrep™ SP FF. Virus was eluted as a discreet peak in a final formulation of 22 mM sodium citrate, 13.1 mM citric acid and 200 mM sodium chloride, at ~pH 4.8 (SP Peak or Purified Bulk), and sterile filtered. The virus was further concentrated by Tangential Flow Filtration using a 100K NMWC Midgee Hollow Fiber cartridge (GE Healthcare Life Sciences) and filter sterilized (Final stock). Alternatively, purified bulks were concentrated using Apollo® 20 mL 150 kDa Concentrators (Orbital Biosciences, Topsfield, Mass.).

rAAV-Specific Assays

Vector genome titer. Vector genome titers were obtained by quantitative Real-time PCR (Q-PCR) as previously described[12]. Vector stocks were submitted to RNase-free DNase I digestion (New England BioLabs, Ipswich, Mass.) (20 U/mL, 30 minutes, 37° C.) and diluted 6 times in RNAse-DNAse-free water (Gibco) using a 5-fold dilution scheme ($5 \times 10^2$ fold to $1.56 \times 10^6$ fold). PCR reactions were prepared according to manufacturer's instructions: 1×iQ SYBR Green Supermix (Bio-Rad, Hercules, Calif.), 200 nM UF5-3F and UF5-3R primers, 95° C. 10 minutes, 95° C. 10 seconds, 62° C. 30 seconds, 40 cycles (CFX Connect Real-Time System, Bio-Rad). A standard curve was prepared using pTR-UF5 plasmid. For AAV-Des-GAA, Desmin promoter-specific primers were used in combination with a standard curved prepared with pTR-Des-GAA plasmid.

Transduction assay. Ad5-infected C12 cells were infected in 96-well plates by serial dilutions of the rAAV-containing samples. After 42-48 hours, GFP-expressing cells were visually counted under microscopy and titer calculated.

Identity and purity assay. Purity and capsid amount were assessed by Coomassie staining. Stocks were diluted $1 \times 10^{13}$ vg/mL in rAAV9 excipient (elution buffer) and $2 \times 10^{11}$ vg were separated on a 10% SDS-polyacrylamide gel (Bio-Rad). Gel was stained using GelCode™ Blue (Pierce, ThermoFisher) and scanned. Purity was assessed by quantification of VP1/2/3 and expressed as a percentage of total protein detected and quantified by the imaging software Quantity One® (Bio-Rad).

Western blotting. Purified vector preparations were prepared like the Coomassie staining except that $1 \times 10^{10}$ vg vector genomes were separated on a 10% SDS-polyacrylamide gel (Bio-Rad) and transferred to nitrocellulose membrane. AAV capsid were detected using an anti-AAV capsid antibody (ARP American Research Product, Waltham, Mass.) at a dilution of 1:2000 and a goat anti-mouse infrared conjugated secondary at 1:10,000. Blots were visualized and quantified using an infrared imaging system and accompanying software (LiCor, Lincoln, Nebr.).

Flow cytometry. EXPI293F™ were infected at an MOI of 2 with rHSV-GFP alone or co-infected with both rHSV-UF5 and rHSV-AAV9 at an MOI of 2 and 4, respectively. At 48 hours post-infection, cells were collected by centrifugation, washed in PBS, and suspended in 1% paraformaldehyde in PBS. Cell sorting for GFP expression was performed on a FACS10 Calibur (BD Biosciences, San Jose, Calif.) and analyzed using CellQuest Version 3.3. Each experiment was run with 10,000 cells and uninfected EXPI293F™ were compared as a control. Total GFP positive cells and GFP intensity was measured.

Statistical analysis. GraphPad Prism software (GraphPad, La Jolla, Calif.) was used to analyze differences between groups utilizing a one-way ANOVA followed by Dunnett's post-test for group comparison. P-values <0.05 were considered statistically significant.

Increased Sodium Chloride Concentration Improves rHSV-Based rAAV Titers in EXPI293F™ Suspension Cells This protocol for the production of rAAV9 in suspension was built upon the one developed for adherent HEK293 with the following changes: EXPI293F™ cells were counted and homogenized in fresh medium at a concentration of $1 \times 10^6$ cell/mL on the day of infection. The inoculum containing the rHSV stocks (rHSV-UF5 (GFP), and rHSV-AAV9) in appropriate amounts was prepared in the growth medium and directly added to the cell suspension culture. Similar to the adherent protocol, rAAV production was carried out for 48 hours, cell harvested by centrifugation, and the media discarded. Experiments to determine effect of salt were performed at small-scale (50 mL cell suspension, $5 \times 10^7$ cells) by directly analyzing rAAV vector genome and infectious titers from the cell crude lysates to enable quick screening of the various parameters assessed.

During preliminary experiments, it was observed that despite maintaining the multiplicity of infection (MOI) across the experiments, the yields of rAAV9-GFP vector varied substantially depending on the rHSV stocks used, with rHSV stocks at lower titers often resulting in higher rAAV9 yields. Since this was consistently observed across multiple lots of rHSV, it was ruled out that the relatively high variability of the PFU assay (±50%) would be the explanation, although it may have contributed. It was then reasoned that since lower rHSV titer resulted in increased volume of each of the rHSV stocks added to the inoculum, a component of the rHSV stock matrix may impact rAAV production. rHSV stock matrix was composed of 1×DMEM containing 5% FBS, 5% glycerol, and 600 mM sodium chloride (NaCl) (see Materials and Methods). To evaluate the direct impact of the rHSV-matrix on rAAV production, suspension EXPI293F™ cells were co-infected with constant volumes of the "viral inoculum" containing rHSV-GFP and rHSV-AAV9 at an MOI of 2:4 respectively, but varying volumes of a mock matrix (matrix inoculum) prepared with 1×DMEM, 5% FBS, 5% glycerol and 600 mM NaCl. The matrix inoculum was supplemented so that the volume of the viral inoculum plus the matrix inoculum would represent 5, 10, 15, 20 or 25% of the total growth medium (vol:vol) in the flask. Interestingly, infection in rHSV+matrix inoculum at a final concentration of 5-15% of the total volume resulted in a significant increase in rAAV production, with more than a 5-fold increase in rAAV total infectious units obtained at 10% final rHSV matrix concentration when compared to the same condition not supplemented with the matrix inoculum (FIG. 4A). Upon adjusting the rHSV inoculum with the HSV-free matrix to a final concentration of the total production volume, the "HSV Matrix" inoculum added to the cell culture was at 0.5% FBS, 0.5% glycerol and 60 mM final concentration of sodium chloride at the time of rHSV infection. Concentration of the rHSV matrix above 20% of total volume resulted in a net decrease of rAAV production, suggesting a drastic impact on cell metabolism or viability, which was not further characterized.

The next aim was to determine more specifically which of the three main components of the HSV-vector matrix, FBS, glycerol or salt, or which combination of these components, was responsible for the increase in rAAV production. The same procedure design as above was followed, with EXPI293F™ cells infected at a MOI of 2:4 (constant viral inoculum volume) but supplemented with different ratio of matrices made of 1×EXPI™ grow medium supplemented with either 5% FBS, 5% glycerol, or 600 mM sodium chloride alone, or a combination of each component. Each of the different matrices were added to the production culture to reach a final concentration of 15% of the final volume. All media supplementations containing sodium chloride showed an increase in rAAV production that was similar to increases seen when all three components were added, regardless of whether this was prepared in EXPI™ or DMEM media (4.5-6.5 fold; FIG. 4B; DMEM results not shown). A similar experiment was performed where all components were diluted in 1×DMEM instead of EXPI™ media. Comparable results were obtained to those shown in FIG. 4B, suggesting components of the DMEM had little impact on rAAV production. Together, this demonstrated that 60-90 mM sodium chloride in the production media resulted in a significant increase in rAAV production utilizing the rHSV co-infection method in EXPI293F™ cells.

The dose curve study was repeated using only sodium chloride. EXPI™ cells were co-infected in the presence of increasing amounts of sodium chloride alone, ranging from 30-90 mM of supplemented concentrations. A 2 to 4.3-fold increase was seen in total capsid proteins, transducing units, and vector genomes when media was supplemented at the optimal concentration of 60 mM sodium chloride (FIG. 4C to FIG. 4E). Total vector genome and transducing unit values are shown in Table 5. This further confirmed that the presence of other additives (FBS, glycerol) was not impacting the effect of sodium chloride on vector production when tested at lower or higher concentrations. To evaluate if increased salt concentrations damaged cells or resulted in the release of rAAV into the supernatant, virus production in cell pellets and supernatants were evaluated at 24, 48, and 72 hours following infection in either media alone or supplemented with 60 mM of sodium chloride. There was no significant difference in total transducing units obtained from lysis of cell pellets at either time point (FIG. 4F). Measurement of transducing units in the supernatant demonstrated less than 2% of total virus produced was released outside of cells at 24 to 72-hour post-transduction. FIGS. 4G and 4H show the impact of sodium chloride concentration on the expression of the gene of interest. There was no significant difference in the number of cells transduced by HSV-UF5 (88-90%) but there was a 3-4 fold increase in the intensity of GFP expression in cells tranduced in media supplemented with 0.6M NaCl to 5% and 10%. (FIG. 4G). rAAV9 capsid protein were measured at 24 and 48 hours following transduction with only HSV-AAV9 and increasing percentages of 0.6M NaCl. In all time points, the greatest increase in capsid protein production was seen in cells infected with media containing 10% 0.6 M NaCl (FIG. 4H).

TABLE 5

Impact of sodium chloride on production of multiple rAAV serotypes.

| | rAAV2-GFP | | rAAV5-GFP | | rAAV9-GFP | |
| --- | --- | --- | --- | --- | --- | --- |
| | Expi293F ™ Media | Media + 60 mM NaCL | Expi293F ™ Media | Media + 60 mM NaCL | Expi293F ™ Media | Media + 60 mM NaCL |
| Total VG | $9.31 \times 10^{11}$ | $2.32 \times 10^{12}$ | $3.14 \times 10^{12}$ | $1.10 \times 10^{13}$ | $1.64 \times 10^{12}$ | $8.92 \times 10^{12}$ |
| VG/cell | $1.86 \times 10^{4}$ | $4.65 \times 10^{4}$ | $6.29 \times 10^{4}$ | $2.20 \times 10^{5}$ | $3.29 \times 10^{4}$ | $1.78 \times 10^{5}$ |
| Total TU | $2.43 \times 10^{10}$ | $1.06 \times 10^{11}$ | $1.88 \times 10^{7}$ | $9.75 \times 10^{7}$ | $4.48 \times 10^{7}$ | $2.20 \times 10^{8}$ |
| TU/cell | 485 | 2110 | 0.38 | 1.95 | 0.90 | 4.40 |
| Ratio VG:TU | 40.26 | 26.74 | $1.76 \times 10^{5}$ | $1.14 \times 10^{5}$ | $4.39 \times 10^{4}$ | $4.05 \times 10^{4}$ |

A range of MOI and ratios between the two rHSVs were tested, keeping in mind that based on observations describe above, the concentration of sodium chloride may impact the assessment of MOI directly related to the volume of rHSV stocks added to the production media. Therefore, infection with a combination of MOIs including 1, 2, and 4 for rHSV-GFP and 2, 4, 8, 10, and 12 for rHSV-AAV9 with sodium chloride adjusted to the optimal concentration (10% or 60 mM) were performed. No major differences were observed with any combination of rHSV co-infection in the MOI range studied (P>0.6 for all). Similar results were observed for EXPI293F™ and BHK cells infected with HSV-UF5 and HSV-AAV9 at various MOIs (FIG. 3). For rHSV-GFP and rHSV-AAV9, results indicated that an MOI of 1 to 2 of the rHSV-AAV and MOI of 4 to 10 were optimal with regards to rAAV titer. All production runs in this study were therefore then performed using an MOI ratio of 2:4 for HSV-GFP:HSV-AAV9. This was also in line with MOI published for sBHK[13]. This suggested that an improvement with increased MOI of virus may be due in part to the increase salt concentration in the media obtained from utilizing a higher volume of rHSV vector, not due to the increase in total vector particles.

The next aim was to explore at what point during rHSV infection or rAAV production cycle was the addition of sodium chloride critical for increased vector production. Following infection with rHSV-GFP alone or co-infection with rHSV-GFP and rHSV-AAV9, EXPI293F™ cells were analyzed at 48 hours post-transduction by flow cytometry. There was no significant difference in GFP-positive cells, with greater than 95% of infected cells expressing GFP in both normal and sodium chloride supplemented cultures (FIG. 5A). An approximate 2 to 3-fold increase in GFP expression was observed in cells infected with rHSV-GFP alone and those infected with both rHSV-GFP and rHSV-AAV9 in the presence of sodium chloride as measured flow cytometry (FIG. 5B). Together, these data strongly suggested that the increase in rAAV titer was not directly correlated to an increase in rHSV-mediated cell transduction but instead impacted viral gene expression and/or production of rAAV.

Last, a time course experiment was performed where salt was added at different time point and/or removed at different time points. EXPI293F™ cells were co-infected with rHSV-AAV9 and rHSV-GFP at an MOI of 2:4. Cells were infected in normal EXPI293F™ media or media supplemented with 60 mM sodium chloride and either incubated 48 hours without media change, or after 4-6 hours, media was changed to either regular or sodium chloride containing EXPI293F™ media. Each combination represented either the presence or absence of salt at the time of infection only, during viral production only, or during the entire infection and production process. Increases in rAAV9 transducing units and capsid proteins were observed in infection conditions where increased sodium chloride was present 4-6 hours post-transduction, regardless of whether the media was changed or the rHSV was left throughout the infection process (FIG. 5C). No increase was seen when media was changed 4-6 hours post-transduction to EXPI293F™ media without sodium chloride. The necessity of sodium chloride during viral production, but not entry, was confirmed in 3 L cultures. Sodium chloride was present either at rHSV infection, added 6 hours post-infection, or added when media was changed at 6 hours to media supplemented with 60 mM sodium chloride. A significant decrease was seen in vector genomes in the cultures where media changes did occur, but no significant change in vector genomes or transducing units was observed when sodium chloride was added 6 hours following rHSV infection (FIG. 5E and FIG. 5F). This data demonstrated that increasing salt concentrations at the time of rAAV production significantly improved viral titers in EXPI293F™ cells and suggested that the salt did not improve HSV entry itself.

Altogether, these data showed that increasing sodium chloride concentration in the media at the time of rAAV production increased rAAV titers when utilizing the rHSV co-infection method in EXPI293™. This demonstrated optimal vector production could be achieved by 48 hours post-infection in cell harvests with minimal release of vector into supernatant.

Sodium Chloride-Mediated Increase in rAAV Production Occurs in Other rAAV Serotypes and Transgenes and for Other Cell Lines Impact of sodium chloride on rAAV production utilizing other rAAV serotypes, other genes of interest, and other cell lines were investigated next. Production of rAAV2-GFP, AAV5-GFP, and rAAV9-GAA were tested in EXPI293F™ cells in media supplemented with 0-90 mM sodium chloride. For rAAV2-GFP and rAAV5-GFP, there was a 4.3 to 5.2-fold increase in transducing units and 2.3 to 2.5-fold increase in vector genomes, respectively, when media was supplemented with 60 mM sodium chloride (FIG. 6A and FIG. 6B). A 3-fold increase in rAAV9-GAA vector genomes was observed with media supplemented to 60 mM with sodium chloride (FIG. 6B). Total vector genome and transducing unit values are shown in Table 5. This data demonstrated that sodium chloride media adjustment improved rAAV production in other AAV serotypes and genes of interest.

Previous work characterizing rHSV co-infection in suspension was performed on BHK cells in DMEM supplemented with FBS[13]. To further compare viral production and sodium chloride media supplementation, BHK cells grown in DMEM containing 5% FBS and BHK cells adapted to grown in SFM4Transfx serum-free media (BHK-SFX) were infected with rHSV-AAV9 and rHSV-GFP in the presence of increasing amounts of sodium chloride. Adaptation of BHK cells to serum free media showed similar replication and growth characteristics as BHK grown DMEM/FBS and the adaption method is described in Materials and Methods section. Similar to EXPI293F™ cells, BHK cells grown in DMEM with 5% FBS showed a significant, 2.2-fold increase in transducing units when media was supplemented with 60 mM sodium chloride (p<0.001; FIG. 6C). Interestingly, BHK cells adapted to grown in serum-free media showed a 5.2-fold increase in rAAV9 transducing units with only 30 mM sodium chloride (FIG. 6C). Total vector genomes were increase 2-3.5-fold following supplementation with optimal concentrations of salt in BHK cells grown in DMEM with 5% FBS and serum free media, respectively (FIG. 6D). Both EXPI293F™ and BHK cells grown in serum-free media without additional sodium chloride produced 1.6 and 5-fold less virus than BHK cells grown in DMEM with 5% FBS, suggesting lower yields by rHSV in serum-free platforms. Supplementing these serum-free media with salt improved viral production to levels approximately equivalent (BHK-SFX) or 2.8-fold greater (EXPI293F™) than BHK in DMEM/FBS, suggesting addition of sodium chloride in the rHSV production process can improve lower rAAV yields that can be observed during rAAV production in serum-free media[3]. Overall, these data showed that increasing sodium chloride concentrations in the rHSV platform improved rAAV vector production across multiple serotypes, transgenes, cell lines, and medias.

The Production System Using EXPI293™ is Highly Scalable

The next aim was to evaluate the scalability of this novel suspension production procedure by evaluating total viral production in crude lysates. Analyzing Benzonase®-treated crude lysates was critical to assess total production capabilities independently of the purification processes that may vary across laboratories and even across the different AAV serotypes. FIG. 7A to FIG. 7C show the total transducing unit and vector genome yields as a function of working production volumes comprised between 50 mL and 3 L, or a 60-fold scale-up. The increase in yield was relatively linear to the volume increase for scales up to 0.5 L with an average of approximately 7-fold increase in transducing unit (TU) when compared to 50 mL (FIG. 7A). However, the yield increase was about twice as much as the increase in volume from 50 mL to 1 L (~40-fold) and to 3 L (~155-fold). The highest yields were obtained from 3 L working volumes for rAAV-GFP with an average of $1.24 \times 10^{15}$ vg±$4.66 \times 10^{14}$ (n=4) or $4.12 \times 10^{14}$ vg/L±$1.55 \times 10^{14}$ in crude lysates, an 8-fold increase as compared to 1 L, and a 27-fold increase when compared to 0.5 L (FIG. 8B). This resulted in an average of $4.12 \times 10^5$ vg/cell±$1.55 \times 10^5$ (FIG. 7C). The increase in infectious units paralleled the particle titers, with an average of $3.16 \times 10^{10}$±$8.90 \times 10^9$ TU (transducing units) for the 3 L crudes as compared to $1.05 \times 10^9$±$5.74 \times 10^8$ (n=4) for 0.5 L, an ~30-fold increase. Yields for rAAV9-GAA were more consistent with expected scaled-up increase with an average of $3.97 \times 10^{14}$ total vector genomes per 3 L or $1.2 \times 10^{14}$ vector genomes per liter culture (n=2; FIG. 7B). A better growth environment in the 5 L flask, utilized to perform the 3 L working production batches, may explain this more favorable scale. The ratio of media to the flask volume, the shaking speed and/or the flask shape may promote oxygenation, reduce cell shear or improve virus/cell contact. As observed at smaller scales, the infectivity of the rAAV9 batches was maintained throughout the scaling process with a ratio VG:TU of $3.88 \times 10^4$±$1.88 \times 10^4$ (11 independent runs at 0.5, 1 and 3 L).

The Biological Quality of the rAAV9 Vectors Produced by the Higher Salt-Containing Suspension System is Maintained Although manufacturing yields were often provided from crude harvests to enable side-by-side comparison across different production methods, it was essential to carefully characterize the final product to not only support the results obtained in crude samples, but more importantly to rule out any potential bias from the presence of cellular and viral bio-products (for instance HEK293 or HSV proteins). For this purpose, five independent and fully purified vector batches prepared from EXPI293F™ were fully characterized with respect to physical and biological parameters. Stocks prepared in the presence or absence of salt supplementation were assessed side-by-side, and compared to preparations that were produced on adherent HEK293 by HSV co-infection, as previously described[12]. Highly concentrated stocks were generated using the GMP-like purification method[19].

Sodium chloride media supplementation was also tested in the previously published adherent HEK293 rHSV-based rAAV9 optimized production method[12]. When DMEM was supplemented with 60 or 90 mM sodium chloride, there was a significant, 1.6 and 2.2-fold increase in rAAV vector genomes and transducing units, respectively (FIG. 8A to FIG. 8B, black bars, p<0.05). While this confirmed that sodium chloride also increased vector production in a HEK293 adherent platform, this suggested that the sodium chloride-mediated increase in vector production was more robust in the suspension format. The impact of sodium chloride supplementation was next tested in the traditional transfection-mediated rAAV9 production platform. HEK293 cells were co-transfected with pTR-UF5 (GFP) and pDG-UF9-KanR plasmids and 60 mM salt was supplemented at the time of transfection or 6 hours post-transfection[12]. Salt supplementation resulted in a dramatic decrease in rAAV yields. This suggested that the impact of sodium chloride may be specific to the rHSV production method, or that further experimentation is required to adapt it to the adherent format or to other AAV production methods.

Total vector genome yields per production unit for adherent HEK293 and suspension EXPI293F™ cells are reported in FIG. 8A. The total yield from five independent salt-optimized suspension runs of rAAV9-GFP in EXPI293F™ cells averaged at $3.5 \times 10^{14}$ vg±$1.7 \times 10^{14}$ or $1.17 \times 10^{14}$ vg/L±$5.66 \times 10^{13}$ of suspension culture. Overall, the yields in EXPI293F™ cells appeared approximately 3-fold superior to yields obtained in adherent HEK293 cells infected in the presence of increased sodium chloride concentrations ($1.15 \times 10^{14}$ vg per CS10®±$2.97 \times 10^{13}$, n=6; FIG. 4A). This resulted in an average of $1.17 \times 10^5$ vg/cell in EXPI293F™ cells compared to $5.14 \times 10^4$ vg/cell and $3.87 \times 10^4$ vg/cell for the same rAAV9-GFP construct in adherent HEK293 cells with and without sodium chloride supplementation, respectively (FIG. 8C). The final titers for rAAV9-GFP produced in EXPI293F™ cells ranged between $2.6 \times 10^{13}$ vg/mL and $6.1 \times 10^{13}$ vg/mL. Some of the final stocks produced on HEK293 were concentrated using a spin device in lieu of a Hollow Fiber cartridge (tangential flow filtration). Spin concentration resulted in about 20% loss of the vector while the TFF method supported a 100% recovery of the biological material. This may account for slightly underestimated yields for the HEK293. More importantly, the infectivity of the vector preparations produced with the suspension platform and those produced in increased sodium chloride media was highly comparable, if not improved, to the ones of vectors produced using the adherent platform, with averaged ratio VG:TU of $2.07 \times 10^4$ in EXPI293F™ cells versus $2.18 \times 10^4$ and $3.39 \times 10^4$ in adherent HEK293 cells with and without sodium chloride supplementation, respectively (FIG. 8E). Therefore, salt supplementation did not affect the infectivity of the rAAV9 particles independently of the production format.

Finally, overall purity and capsid ratios in the fully purified vector preparations were assessed. Identical amounts of vector genomes were analyzed by Coomassie staining and Western blotting. FIG. 8F shows that the overall capsid load is similar whether the rAAV9 stocks were prepared in EXPI293F™ or HEK293, or in the presence or absence of salt supplementation. This observation was confirmed by Western blot analysis. Therefore, the ratio full-versus-empty capsids was not impacted by the suspension production platform nor the salt supplementation. The purity was greater than 90% in all cases with little detection of non-AAV9 by-product detected at the amounts tested.

Salt Supplementation is a Strategy to Boost rAAV Production that Works for Different AAV Serotypes and Genes to be Packaged and at Different Scales.

FIGS. 10 and 11 shows that supplementation of producer media with 60 mM NaCl resulted in an increase in rAAV production for AAV or serotypes 2, 5 and 9, and for packaging of both GFP and Des-GAA genes.

FIG. 12 shows that salt can be supplemented at the time of infection of cells and up to at least 6 hours after infection, without affecting the yield improvement over not supplementing with salt.

Also noted is that simultaneous coinfection is not required for optimal AAV production (FIG. 13).

Further, the quality of rAAV9-GFP stocks is improved when produced in the HSV system in combination with salt supplementation and suspension-adapted EXPI293F™ cells (FIG. 14).

The strategy illustrated herein to improve rAAV production yields is applicable at various production scales (FIG. 15).

rAAV Vector Quality

Salt supplementation was also found to affect rAAV vector quality (FIG. 16). Both vector degradation and contamination of rAAV preparations by HEK293 proteins and HSV proteins (when infection by HSV was used) were lower in EXPI293F cells supplemented with salt compared to HEK cells that were transfected, HEK cells that were infected with HSV and HEK cells that were infected with HSV and supplemented with salt (FIGS. 16B and 16C). Degradation of rAAV vectors was also lower in EXPI293F cells supplemented with salt compared to HEK cells that were transfected, HEK cells that were infected with HSV and HEK cells that were infected with HSV and supplemented with salt (FIG. 16A).

Accordingly, reported in this Example is the production of rAAV utilizing the rHSV system in suspension HEK293 cells (EXPI293F™) grown in serum and animal component-free media. Through adjustment of salt concentration in the media and adjustment of infection conditions, titers greater than $1\times10^{14}$ vector genomes per liter (vg/L) were observed in purified rAAV stocks produced in EXPI293F™ cells. Furthermore, this system allowed for high titer production of multiple rAAV serotypes (2, 5, and 9) as well as multiple transgenes (GFP and acid alpha-glucosidase (GAA)). A proportional increase in vector production was observed as this method was scaled, with a final 3 L shaker flask production yielding an excess of $1\times10^{15}$ vg in crude cell harvests and an average of $3.5\times10^{14}$ total vg of purified rAAV9 material, resulting in greater than $1\times10^5$ vg/cell. These results support the use of this rHSV-based rAAV production method for large scale pre-clinical and clinical vector production.

The increased interest in rAAV as a therapeutic vector and commercial product has highlighted the need for large-scale manufacturing method for vector production. While rAAV vectors were relatively easy to make for research use, large-scale manufacturing methods that can provide high titer and high purity vector continue to lag behind the immense clinical demand. It is without surprise that both industry and academic laboratories, often as a collaborative effort, are poised for an unprecedented investment of resources toward this common goal. The study in this Example details a rHSV-based production method that produced high titer rAAV vectors in a serum and animal component free suspension EXPI293F™ platform. It is believed that this is the first time that a simple component such sodium chloride has shown to have a dramatic effect on rAAV production in a suspension platform. With optimal sodium chloride concentrations in the production media, increased vector titers were achieved for multiple rAAV serotypes and transgenes.

The exact mechanism for how sodium chloride increases rAAV production was not fully investigated since the primary goal was to establish an efficient, robust and attractive method to produce rAAV. Further, little is known or documented in the literature about sodium chloride specific impact on rHSV or rAAV viral cycles. This data sheds some light on possible biological mechanisms affected by sodium chloride. Concentrations up to 0.3 M of sodium chloride was reported to increase specific binding of HSV1 KOS strain to GMK-AH1 cells[20]. However, this data suggests that HSV binding and/or entry may not be significantly impacted. First, a flow cytometry analysis showed that the number of rHSV-GFP-infected EXPI293F™ cells was similar independent of the sodium chloride concentration. Second, it was shown that sodium chloride could be added up to 6 hours after inoculation of rHSV to the production medium with minimal impact on rAAV production. Interestingly, the flow cytometry analysis did reveal an increase in GFP expression in cells infected in the presence of optimal amounts of sodium chloride. This observation suggested that salt may directly impact either HSV or AAV gene expression, or both. A study with poliovirus showed that increased potassium chloride concentrations at 6-9 hours post-infection resulted in an increase in viral translation[21]. However, the increase in GFP expression could also be linked to an increase of AAV genome copies upon enhanced replication levels, which could result from either increased helper HSV gene expression or AAV rep and cap gene expression in the infected cells. The latter is supported by western blot analysis showing significantly increased AAV9 capsid expression in salt-optimized conditions. Whether an optimized salt concentration alters the cellular environment and/or improves rAAV production through mechanisms dependent or independent of HSV infection, remains to be further studied. Because higher salt concentration could possibly affect gene expression of either or both HSV and AAV and lead to higher AAV replication and or packaging, increasing salt concentrations as a strategy for improving rAAV yields could be used in methods involving transfection, as well as methods involving infection.

One of the most attractive data set from this study was the overall yields obtained when using the HSV system both in adherent and suspension platforms. Reported here were yields in crude Benzonase®-treated harvests ranging exceeding $3\times10^{14}$ vg/L of production suspension culture, resulting in about $3.5\times10^5$ vg/cell. These yields match and even surpass the highest AAV amount currently demonstrated for other suspension methods, that includes the Baculovirus expression system (BEV) system, the transfection of suspension-adapted HEK293, and HeLa-derived stable cell lines, as previously discussed[12]. The BEV system was able to generate approximately $2.4\times10^{14}$ vg/L in crude Sf9 cell harvests[22], however, because the cell concentration used is 3 to 4-fold higher than the concentration in the media used here, the amount per cell was significantly reduced to $9\times10^4$. The HSV infection method using suspension-adapted BHK cells reported about $1$-$2\times10^{14}$ vg/L in harvests[13]. The transfection in suspension system, also using HEK293 cells, reported yields ranging around $1\times10^{14}$ vg/L or $1\times10^5$ vg/cells, also in crude material[6]. It is unofficially reported that yields may be higher when using stable cell lines. Unfortunately, data are still very scarce in the literature and conclusive comparison to the above-described system could not be formally drawn at this time[9, 23].

When combined with downstream processes, which vary widely depending on the rAAV serotype produced, overall yields of purified material range from $1\times10^{13}$ vg/L for the transfection in suspension HEK293 to maximum $4$-$5\times10^{13}$ vg/L for the BEV[6, 22, 24, 25]. The first clinical AAV production using the HSV system in sBHK was performed by AGTC with final yield approaching $2\times10^{13}$ vg/L or $1\times10^4$ vg/cell[26]. Yields from the serum-free sBHK protocol have not been published. Preclinical and clinical needs to support ongoing trials appeared negligible (less than $5\times10^{13}$ total vg for the entire toxicology study or clinical trial) and did not reflect the method capability[14, 15].

The system reported here is the first to describe a serum-free EXPI293™ platform for the production of rAAV using the rHSV virus. Since the rHSV stocks were produced in a serum-containing medium, it is possible that residual traces of FBS may still be detected in the final product. However, the high concentration of HSV stocks combined to the low MOIs used in this system did result in an overall input of less than 2% vol/vol or FBS concentration largely inferior to 0.1% during production. Further, rAAV was purified from PBS-rinsed cells, which should remove the majority of FBS-derived impurities. The sBHK system also relied on FBS-containing HSV stocks and final test article stocks were shown to contain detectable amounts of BSA[14, 15].

Taken together, for a phase I clinical study, the theoretical production scale to produce $1\times10^{17}$ vg in crude material was calculated, which would equate to approximately $2\times10^{16}$ vg of IND-enabling purified material (assuming ~20% recovery from most downstream processes). As much as 1000 L of cell cultures would be required if using the transfection in suspension HEK293 platform or the HSV/sBHK platform, 400-500 L if using the BEV system, HSV/sBHK or 175-250 L with the EXPI293F™ system. Inversely, the theoretical yields of rAAV9 starting from the minimal amount of raw material generated from seven CS10®-worth viral seed stock (VSS) were extrapolated (also summarized in FIG. 9). HSV working viral banks (~2120 CS10®) would provide raw material in sufficient quantity to infect approximately 2075 CS10® and generate ~$8\times10^{17}$ vg in unprocessed production harvests. The same amounts would suffice to infect approximately 18,678 L of EXPI293™ and generate about $8\times10^{18}$.

In conclusion, solid collection of data offered a three-fold impact toward enabling manufacturing of large-scale high titer and high quality rAAV vectors: 1) a suspension-adapted and highly scalable production platform 2) serum-free production cultures and 3) unique biological quality of the resulting product. While yields vary from construct to construct, this data provides a strong framework toward achievable high yields to support pre-clinical and clinical studies, with an unparalleled flow path toward commercialization-enabling scales. Altogether, this method is poised to facilitate IND-enabling preclinical and clinical studies in a booming interest for AAV-driven gene therapy.

REFERENCES

1. Samulski R J, Muzyczka N. AAV-mediated gene therapy for research and therapeutic purposes. Annual Review of Virology 2014; 1:427-451.
2. Clément N, Grieger J C. Manufacturing of recombinant adeno-associated viral vectors for clinical trials. Molecular Therapy Methods & Clinical Development 2016; 3:16002.
3. Hildinger M, Baldi L, Stettler M et al. High-titer, serum-free production of adeno-associated virus vectors by polyethyleneimine-mediated plasmid transfection in mammalian suspension cells. Biotechnol Lett 2007; 29:1713-1721.
4. Chahal P S, Schulze E, Tran R et al. Production of adeno-associated virus (AAV) serotypes by transient transfection of HEK293 cell suspension cultures for gene delivery. J Virol Methods 2014; 196:163-173.
5. Durocher Y, Pham P L, St-Laurent G et al. Scalable serum-free production of recombinant adeno-associated virus type 2 by transfection of 293 suspension cells. J Virol Methods 2007; 144:32-40.
6. Grieger J C, Soltys S M, Samulski R J. Production of recombinant adeno-associated virus vectors using suspension HEK293 cells and continuous harvest of vector from the culture media for GMP FIX and FLT1 clinical vector. Molecular Therapy 2015.
7. Gao G P, Qu G, Faust L Z et al. High-titer adeno-associated viral vectors from a Rep/Cap cell line and hybrid shuttle virus. Hum Gene Ther 1998; 9:2353-2362.
8. Liu X, Voulgaropoulou F, Chen R et al. Selective Rep-Cap gene amplification as a mechanism for high-titer recombinant AAV production from stable cell lines. Molecular therapy: the journal of the American Society of Gene Therapy 2000; 2:394-403.
9. Martin J, Frederick A, Luo Y et al. Generation and characterization of adeno-associated virus producer cell lines for research and preclinical vector production. Human gene therapy methods 2013; 24:253-269.
10. Martin J N, Wolken N, Brown T et al. Lethal toxicity caused by expression of shRNA in the mouse striatum: implications for therapeutic design. Gene therapy 2011; 18:666-673.
11. Bakker A. AAV vector production: baculovirus vs transient transfection. Human Gene Therapy 2008; 19:1067-1068.
12. Adamson-Small L, Potter M, Falk D J et al. A scalable method for the production of high-titer and high-quality adeno-associated type 9 vectors using the HSV platform. Molecular Therapy—Methods & Clinical Development 2016; 3:16031.
13. Thomas D L, Wang L, Niamke J et al. Scalable recombinant adeno-associated virus production using recombinant herpes simplex virus type 1 coinfection of suspension-adapted mammalian cells. Human gene therapy 2009; 20:861-870.
14. Ye G J, Budzynski E, Sonnentag P et al. Safety and Biodistribution Evaluation in Cynomolgus Macaques of rAAV2tYF-PR1.7-hCNGB3, a Recombinant AAV Vector for Treatment of Achromatopsia. Human gene therapy Clinical development 2016.
15. Ye G J, Budzynski E, Sonnentag P et al. Safety and Biodistribution Evaluation in Cynomolgus Macaques of rAAV2tYF-CB-hRS1, a Recombinant Adeno-Associated Virus Vector Expressing Retinoschisin. Human gene therapy Clinical development 2015; 26:165-176.
16. Conway J E, Zolotukhin S, Muzyczka N et al. Recombinant adeno-associated virus type 2 replication and packaging is entirely supported by a herpes simplex virus type 1 amplicon expressing Rep and Cap. Journal of virology 1997; 71:8780-8789.
17. Conway J E, Rhys C M, Zolotukhin I et al. High-titer recombinant adeno-associated virus production utilizing a recombinant herpes simplex virus type I vector expressing AAV-2 Rep and Cap. Gene Ther 1999; 6:986-993.
18. Falk D J, Soustek M S, Todd A G et al. Comparative impact of AAV and enzyme replacement therapy on respiratory and cardiac function in adult Pompe mice. Molecular Therapy Methods & Clinical Development 2015; 2:15007.
19. Potter M, Lins B, Mietzsch M et al. A simplified purification protocol for recombinant adeno-associated virus vectors. Molecular Therapy—Methods & Clinical Development 2014; 1.

20. Trybala E, Liljeqvist J A, Svennerholm B et al. Herpes simplex virus types 1 and 2 differ in their interaction with heparan sulfate. J Virol 2000; 74:9106-9114.
21. Carrasco L, Otero M J, Castrillo J. Modification of membrane permeability by animal viruses. Pharmacology & therapeutics 1989; 40:171-212.
22. Cecchini S, Virag T, Kotin R M. Reproducible high yields of recombinant adeno-associated virus produced using invertebrate cells in 0.02- to 200-liter cultures. Human gene therapy 2011; 22:1021-1030.
23. Clark K R. Recent advances in recombinant adeno-associated virus vector production. Kidney international 2002; 61:S9-S15.
24. Buclez P-O, Dias Florencio G, Relizani K et al. Rapid, scalable, and low-cost purification of recombinant adeno-associated virus produced by baculovirus expression vector system. Molecular Therapy—Methods & Clinical Development 2016; 3:16035.
25. Mietzsch M, Casteleyn V, Weger S et al. OneBac 2.0: Sf 9 Cell Lines for Production of AAV5 Vectors with Enhanced Infectivity and Minimal Encapsidation of Foreign DNA. Human gene therapy 2015; 26:688-697.
26. Flotte T R, Trapnell B C, Humphries M et al. Phase 2 clinical trial of a recombinant adeno-associated viral vector expressing al-antitrypsin: interim results. Human gene therapy 2011; 22:1239-1247.

This disclosure provides, at least in part:
1. A method of producing rAAV, the method comprising co-infecting suspension-adapted cells with:
   a. a first rHSV encoding a gene of interest flanked by AAV ITRs, and
   b. a second rHSV encoding AAV rep and cap genes.
2. The method of paragraph 1 above, further comprising isolating rAAV from the co-infected cells.
3. The method of paragraphs 1 or 2, wherein the suspension-adapted cells are suspension-adapted HEK293 cells.
4. The method of any one of the paragraphs 1-3, wherein the AAV ITRs are AAV-2 ITRs.
5. The method of any one of the paragraphs 1-4, wherein the AAV ITRs are from AAV-1, AAV-3, AAV-4, AAV-5, AAV-6, AAV-7, AAV-8, AAV-9, or other AAV serotype.
6. The method of any one of the paragraphs 1-5, wherein the AAV cap gene is an AAV-8 or an AAV-9 cap gene.
7. The method of any one of the paragraphs 1-6, wherein the AAV cap gene is from AAV-1, AAV-2, AAV-3, AAV-4, AAV-5, AAV-6, AAV-7, or other AAV serotype.
8. The method of any one of the paragraphs 1-7, wherein the gene of interest encodes a therapeutic protein.
9. The method of any one of the paragraphs 1-8, wherein the gene of interest encodes a protein that is useful for treating a lysosomal storage disease.
10. The method of any one of the paragraphs 1-9, wherein the gene of interest encodes a protein that is useful for treating a neurological disability, a neuromotor deficit, or a neuroskeletal impairment.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

The invention claimed is:

1. A method of producing recombinant AAV (rAAV) in suspension-adapted cells comprised in a medium, the method comprising supplementing the medium with between 5 mM and 200 mM sodium chloride (NaCl) prior to or at the same time as co-infecting the suspension-adapted cells with: a first recombinant herpes simplex virus (rHSV) encoding a gene of interest flanked by AAV inverted terminal repeats (ITRs), and a second rHSV encoding AAV rep and cap genes.

2. The method of claim 1, further comprising diluting or changing the medium after co-infection such that the concentration of NaCl is decreased.

3. The method of claim 2, wherein the diluting or changing the medium occurs 0.5-8 h after co-infection.

4. The method of claim 1, wherein the concentration of supplemented NaCl is between 30 mM and 150 mM.

5. The method of claim 1, wherein the concentration of NaCl is supplemented such that the total concentration of NaCl is between 130 mM and 200 mM.

6. The method of claim 1, wherein the cells are mammalian or insect cells.

7. The method of claim 1, wherein the cells containing the produced rAAV are harvested prior to cell lysis.

8. The method of claim 7, wherein the step of harvesting the cells is performed by centrifugation.

9. The method of claim 1, wherein the AAV ITRs are AAV-2 ITRs.

10. The method of claim 1, wherein the suspension-adapted cells are suspension-adapted HEK293 cells.

11. The method of claim 10, wherein the suspension-adapted HEK293 cells are derived from adherent HEK293 cells.

12. The method of claim 1, further comprising isolating rAAV from the co-infected suspension-adapted cells.

13. The method of claim 4, wherein the concentration of supplemented NaCl is between 60 mM to 90 mM.

14. The method of claim 5, wherein the concentration of NaCl is supplemented such that the total concentration of NaCl is between 135 mM to 180 mM.

* * * * *